(12) United States Patent
Keel et al.

(10) Patent No.: US 8,155,739 B2
(45) Date of Patent: *Apr. 10, 2012

(54) CARDIAC RESYNCHRONIZATION THERAPY OPTIMIZATION USING MECHANICAL DYSSYNCHRONY AND SHORTENING PARAMETERS FROM REALTIME ELECTRODE MOTION TRACKING

(75) Inventors: Allen Keel, San Jose, CA (US); Stuart Rosenberg, Castaic, CA (US); Kyungmoo Ryu, Palmdale, CA (US); Wenbo Hou, Lancaster, CA (US); Thao Thu Nguyen, Bloomington, MN (US); Kjell Noren, Solna (SE); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 442 days.

This patent is subject to a terminal disclaimer.

(21) Appl. No.: 12/476,043

(22) Filed: Jun. 1, 2009

(65) Prior Publication Data

US 2009/0318995 A1   Dec. 24, 2009

Related U.S. Application Data

(60) Provisional application No. 61/074,544, filed on Jun. 20, 2008.

(51) Int. Cl.
*A61N 1/00* (2006.01)

(52) U.S. Cl. .......................................................... 607/9
(58) Field of Classification Search .................. 600/409, 600/420, 424, 425, 508; 607/2, 9, 122
See application file for complete search history.

(56) References Cited

U.S. PATENT DOCUMENTS

| 7,613,500 B2 | 11/2009 | Vass et al. | |
| 2008/0242976 A1* | 10/2008 | Robertson et al. | 600/425 |
| 2008/0319496 A1* | 12/2008 | Zhu et al. | 607/5 |
| 2009/0093857 A1 | 4/2009 | Markowitz et al. | |
| 2009/0287269 A1* | 11/2009 | Hedberg et al. | 607/17 |

FOREIGN PATENT DOCUMENTS

WO   2007111542 A1   10/2007

\* cited by examiner

*Primary Examiner* — George Manuel
*Assistant Examiner* — Robert Wieland

(57) ABSTRACT

Therapy optimization includes tracking electrode motion using an electroanatomic mapping system and generating, based on tracked electrode motion, one or more mechanical dyssynchrony metrics to thereby guide a clinician in therapy optimization (e.g., via optimal electrode sites, optimal therapy parameters, etc.). Such a method may include a vector analysis of electrode motion with respect to factors such as times in cardiac cycle, phases of a cardiac cycle, and therapy conditions, e.g., pacing sites, pacing parameters and pacing or no pacing. Differences in position-with-respect-to-time data for electrodes may also be used to provide measurements of mechanical dyssynchrony.

25 Claims, 19 Drawing Sheets

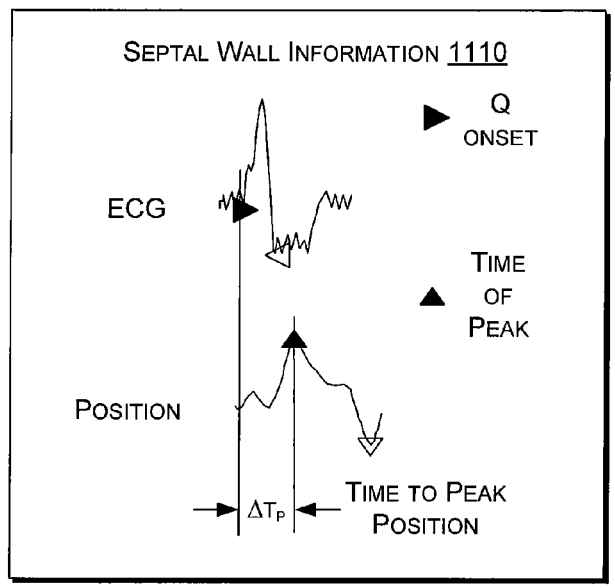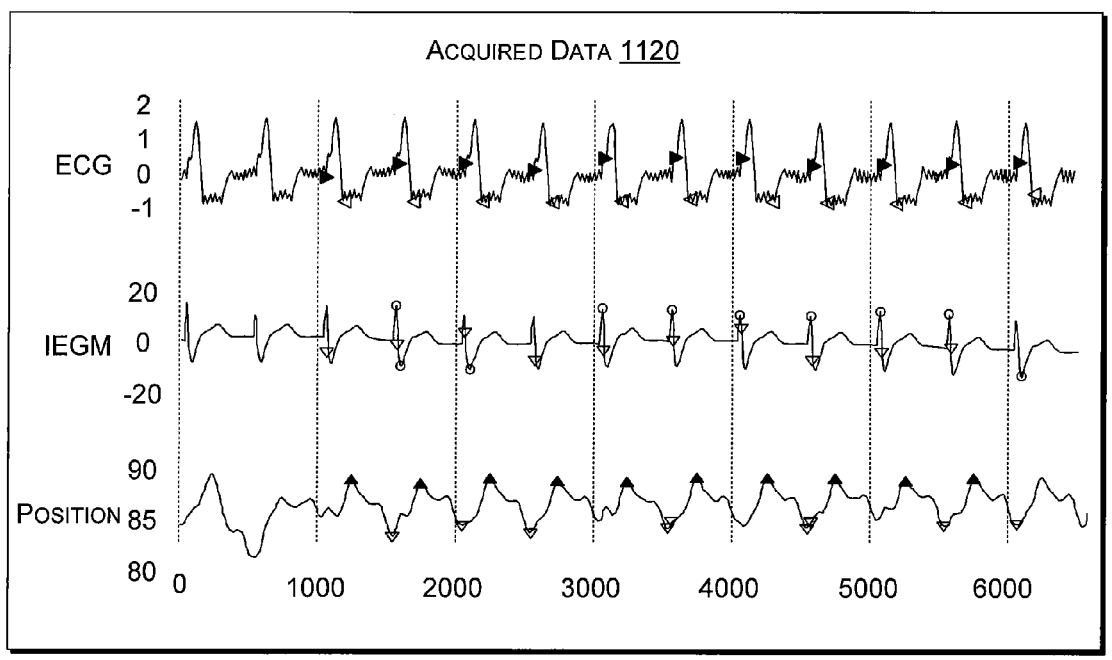
Fig. 11

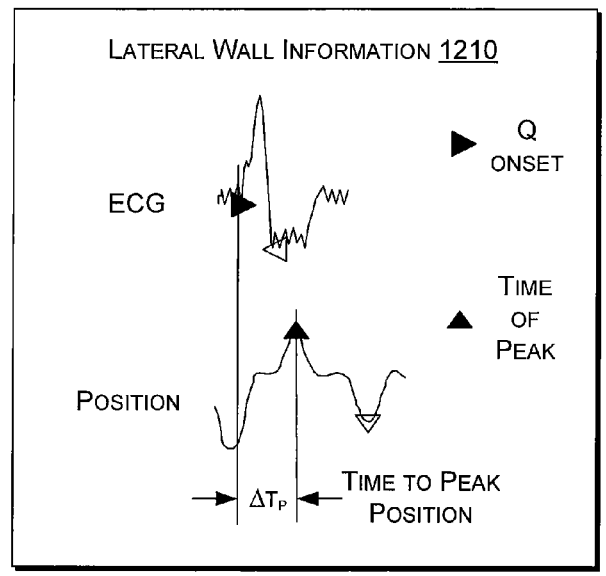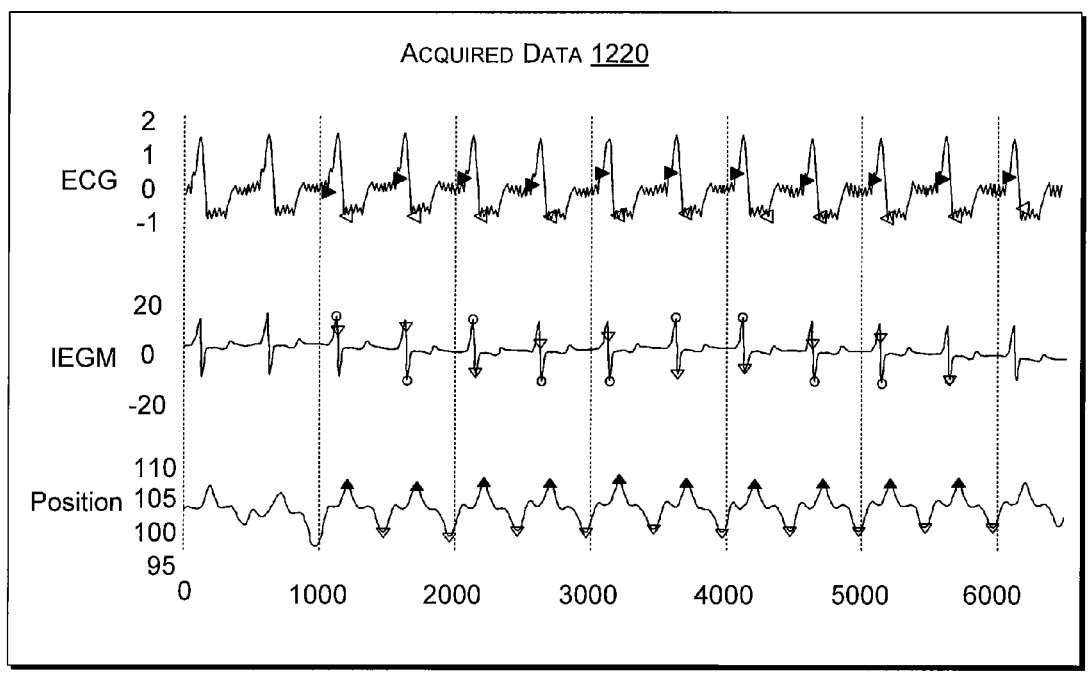
Fig. 12

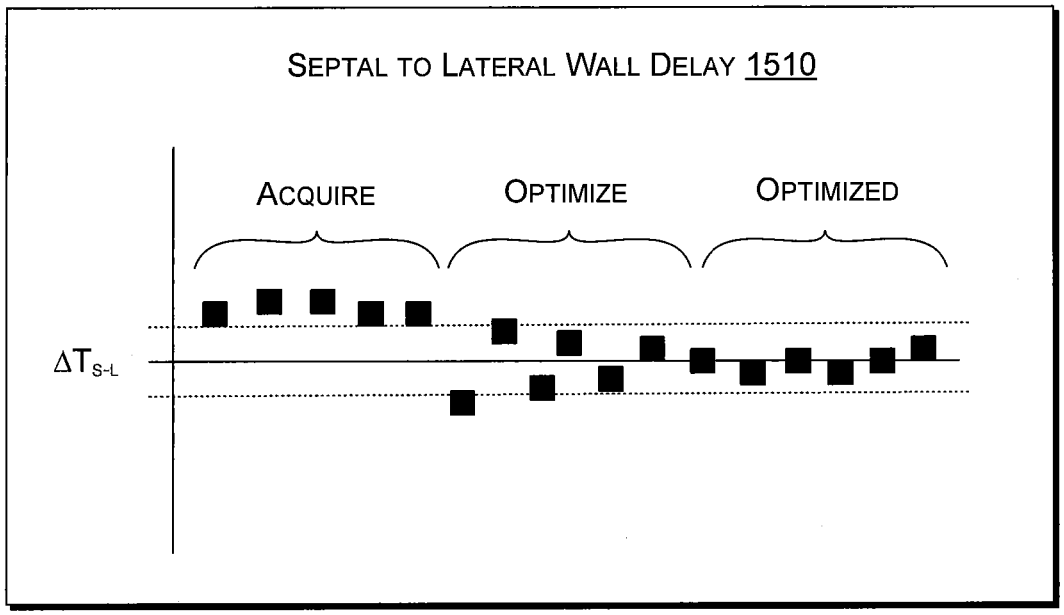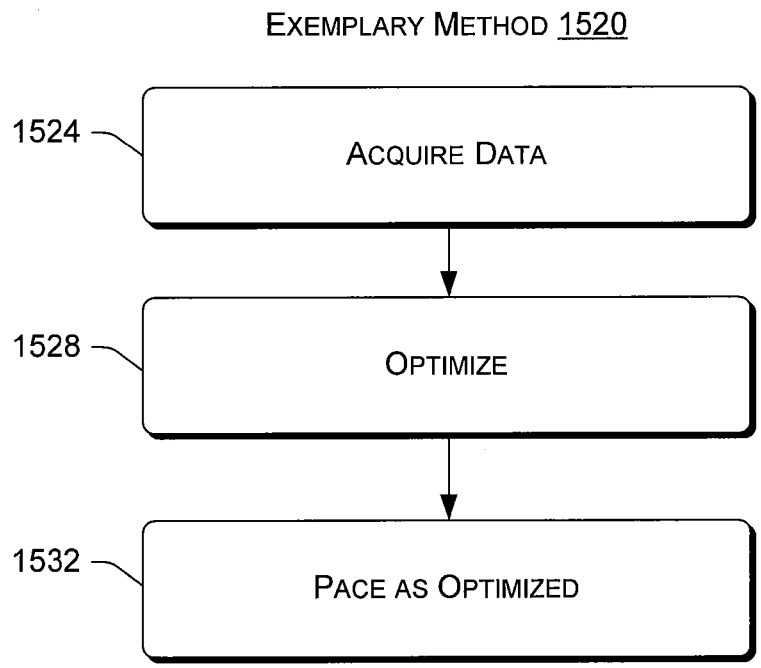
Fig. 15

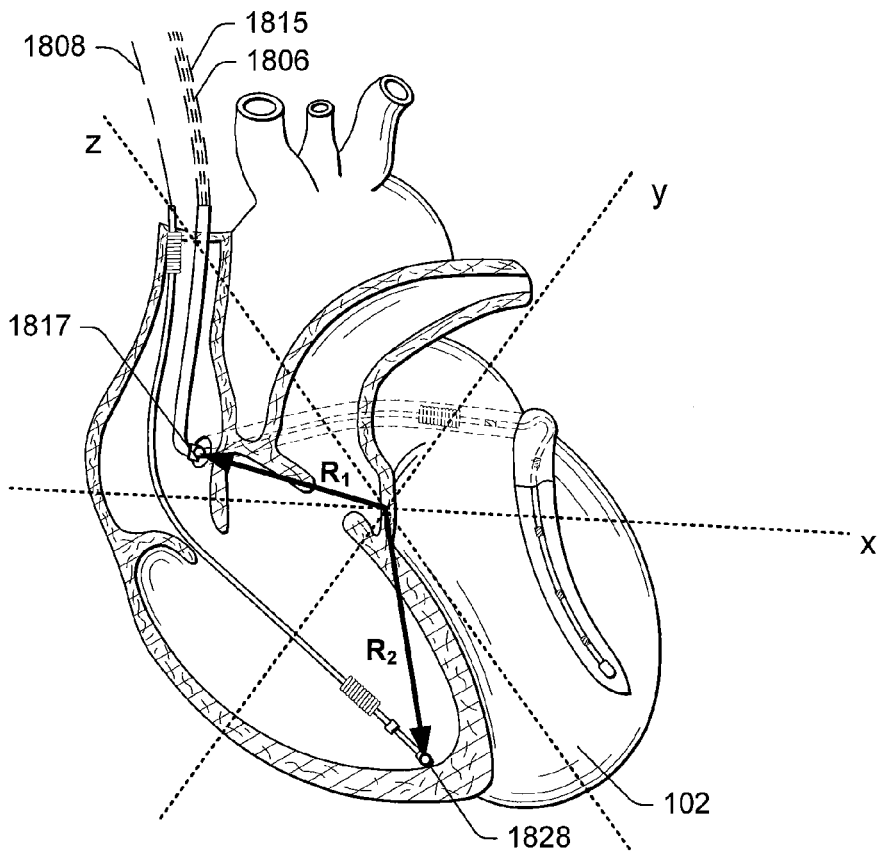
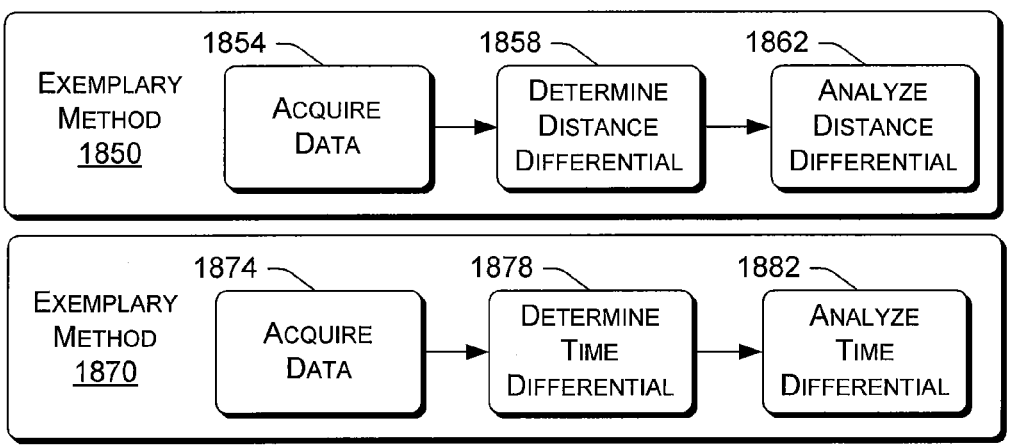
Fig. 18

CARDIAC RESYNCHRONIZATION THERAPY OPTIMIZATION USING MECHANICAL DYSSYNCHRONY AND SHORTENING PARAMETERS FROM REALTIME ELECTRODE MOTION TRACKING

RELATED APPLICATIONS

This patent application claims the benefit of U.S. Provisional Patent Application Ser. No. 61/074,544, entitled "Cardiac Resynchronization Therapy Optimization Using Mechanical Dyssynchrony and Shortening Parameters from Real-time Electrode Motion Tracking," filed Jun. 20, 2008, and is related to U.S. patent application Ser. No. 11/676,108, filed Feb. 16, 2007, entitled "Motion-based Optimization of Cardiac Stimulation Therapy," both of which are incorporated by reference herein.

TECHNICAL FIELD

Subject matter presented herein relates generally to cardiac pacing and/or stimulation therapy. Various examples pertain to mechanisms for optimizing such therapies based at least in part on cardiac motion. Various mechanisms can additionally or alternatively monitor patient condition.

BACKGROUND

Cardiac resynchronization therapy (CRT) aims to improve cardiac performance by synchronizing the ventricles. While the term "synchronization" is used, for some patients, a delay between contraction of the right ventricle and the left ventricle may be optimal. Hence, the term synchronization refers more generally to ventricular timing that improves cardiac performance. A general objective measure of lack of synchrony or dyssynchrony is QRS width representative of contraction of both ventricles. For example, a QRS width greater than about 130 ms may indicate dyssynchrony.

CRT can improve a variety of cardiac performance measures including left ventricular mechanical function, cardiac index, decrease in pulmonary artery pressures, decrease in myocardial oxygen consumption, decrease in dynamic mitral regurgitation, increase in global ejection fraction, decrease in NYHA class, increase in quality of life scores, increase in distance covered during a 6-minute walk test, etc. Effects such as reverse modeling may also be seen, for example, three to six months after initiating CRT. Patients that show such improvements are classified as CRT "responders". However, for a variety of reasons, not all patients respond to CRT. For example, if a left ventricular stimulation lead cannot locate an electrode in a favorable position, then a patient may not respond to CRT.

Often, the ability to respond and the extent of response to CRT depends on an initial set-up of a CRT device in a patient. As described herein, various exemplary technologies aim to improve a clinician's ability to set-up a CRT device at implant (e.g., an acute state) and to optionally optimize device operation thereafter (e.g., a chronic state). In particular, various exemplary techniques include determining one or more specialized dyssynchrony parameters based on cardiac motion information.

SUMMARY

An exemplary method for CRT optimization includes tracking electrode motion using an electroanatomic mapping system and generating, based on tracked electrode motion, one or more mechanical dyssynchrony parameters to thereby guide a clinician in CRT optimization (e.g., via optimal electrode sites, optimal therapy parameters, etc.). Such a method can include a vector analysis of electrode motion with respect to factors such as times in cardiac cycle, phases of a cardiac cycle, pacing sites, pacing parameters, pacing or no pacing, etc. Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

FIG. 11 is a plot of various information related to electrical activity of the heart along with position of a septal wall electrode with respect to time.

FIG. 12 is a plot of various information related to electrical activity of the heart along with position of a lateral wall electrode with respect to time.

FIG. 15 is a plot of a dyssynchrony metric with respect to time and a block diagram of an exemplary method for optimizing a cardiac pacing therapy based at least in part on the dyssynchrony metric.

FIG. 18 is a simplified diagram of the heart having a catheter and leads positioned therein and block diagrams of exemplary methods.

DETAILED DESCRIPTION

Figure 1:
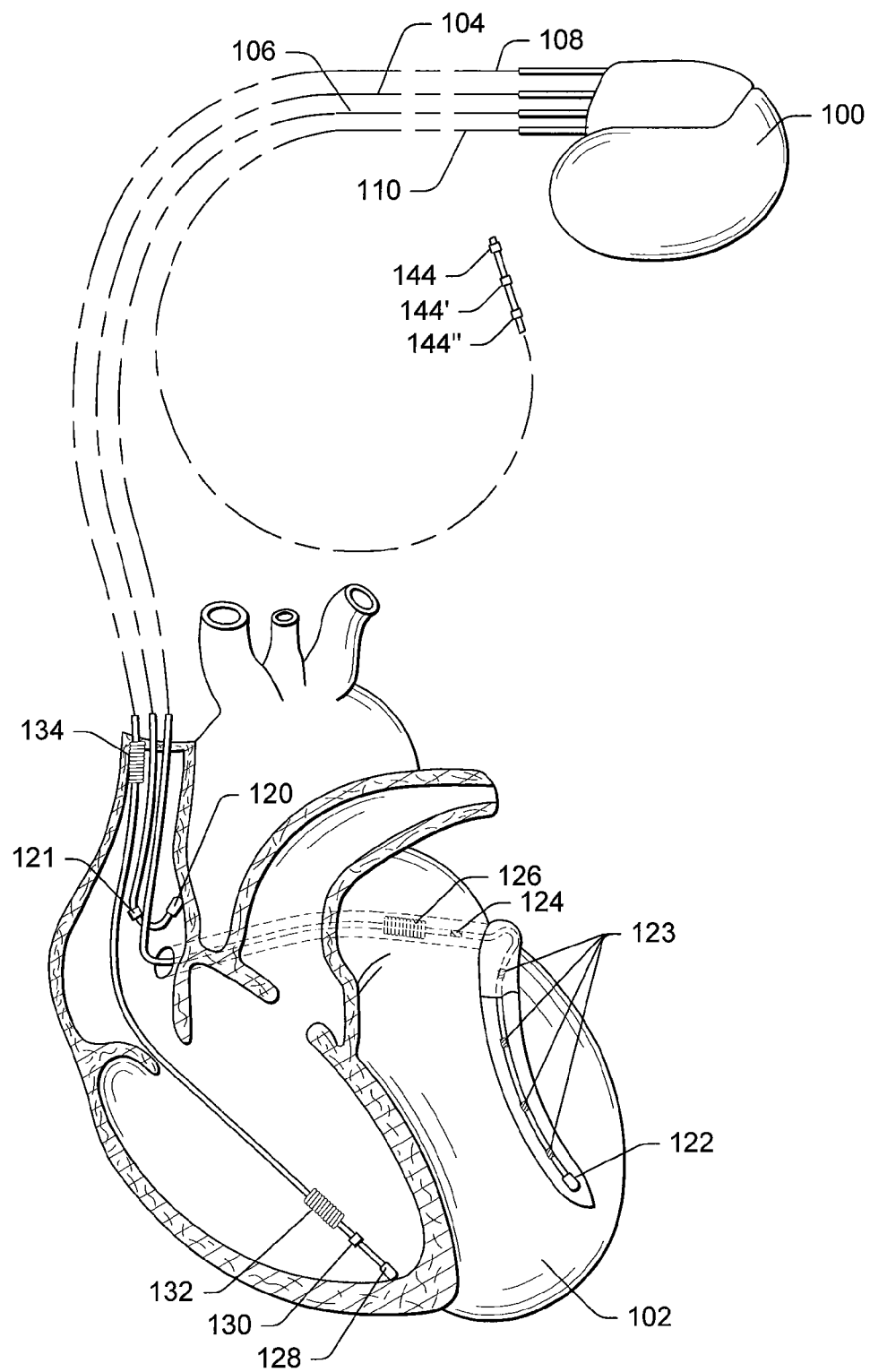
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

As described herein, various exemplary techniques can be used to collect motion data and to compute parameters for use in making decisions as to cardiac pacing therapy and optimization of a cardiac pacing therapy. Various parameters pertain to mechanical dyssynchrony and are, at times, referred to as dyssynchrony metrics, which are based on acquired motion data.

In a clinical trial, acute resynchronization was shown to be a significant parameter in assessing CRT efficacy and long-term outcome[1]. Various methods described herein, build on this clinical finding by formulating specialized techniques and metrics associated with mechanical dyssynchrony. In turn, one or more of these metrics may be used to determine how effective a particular CRT therapy is at any given time.

[1] G B Bleeker, S A Mollema, E R Holman, N Van De Veire, C Ypenburg, E Boersma, E E van der Wall, M J Schalij, J J Bax. "Left Ventricular Resynchronization is Mandatory for Response to Cardiac Resynchronization Therapy: Analysis in Patients with Echocardiographic Evidence of Left Ventricular Dyssynchrony at Baseline." *Circulation* 2007; 116:1440-1448.

As described herein, various exemplary methods can optimize CRT through use of one or more mechanical dyssynchrony parameters that are based on electrode motion as tracked by a localization system (e.g., such as the ENSITE® NAVX® system, St. Jude Medical, Minn.). A localization system can be used not only to locate electrodes for the creation of electroanatomical maps, but also to track the real-time motion of electrodes in one, two or three dimensions. Tracking electrodes in the intracardiac, intravascular, or intra-pericardial space over the course of one or more cardiac cycles can provide an estimate of myocardial motion. Estimated motions, in turn, allow for derivation of one or more mechanical dyssynchrony parameters. As discussed herein, such parameters can be used to assess cardiac performance during CRT implant. Further, such parameters can be used in the optimization of pacing lead location, electrode configuration, AV/VV delays, etc. While various examples pertain to a ventricle or the ventricles, optimization may be performed for an atrium or the atria.

An exemplary stimulation device is described followed by various techniques for measuring electrode motion. Exemplary techniques for measuring motion are then described along with descriptions of exemplary metrics, algorithms for optimizing cardiac pacing therapy and equipment for analysis and programming an implantable device capable of delivering CRT. The drawings and detailed description elucidate details of various distinct mechanical dyssynchrony parameters that may be used singly or in combination during an assessment or an optimization process.

Exemplary Stimulation Device

The techniques described below are intended to be implemented in connection with any device that is configured or configurable to delivery cardiac therapy and/or sense information germane to cardiac therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where for left ventricular stimulation therapies, an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

An exemplary coronary sinus lead 106 can be designed to receive ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using the left atrial ring electrode 124 (e.g., in combination with one or more other electrodes). The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

Figure 2:
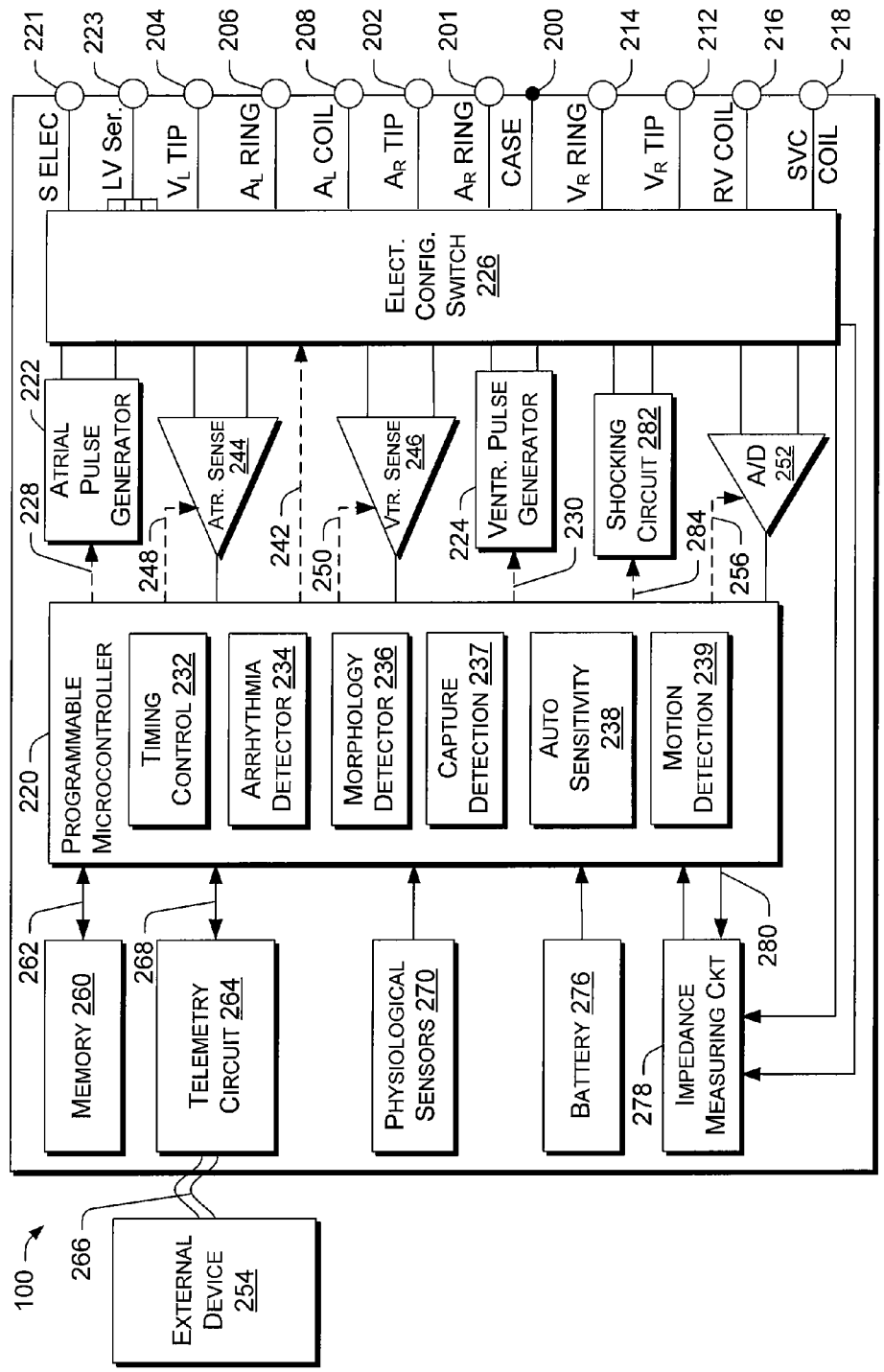
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is for illustration purposes only. Thus, the techniques, methods, etc., described below can be implemented in connection with any suitably configured or configurable device for stimulation and/or sensing. Accordingly, one of skill in the art could readily duplicate, eliminate, or disable the appropriate circuitry in any desired combination to provide a device capable of sensing activity of and/or treating a chamber(s) or a region(s) of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional motion detection module 239. The module 239 may be used for purposes of acquiring motion information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor motion indicative of cardiac mechanics (optionally in relationship to cardiac electrical activity) and may help to optimize cardiac resynchronization therapy. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. Additional configurations are shown in FIG. 11 and described further below. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or a nerve or other tissue stimulation lead through the switch 226 to sample cardiac or other signals across any pair of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to memory 260 by a suitable data/address bus 262, where the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGMs) and other information (e.g., status information relating to the operation of the device 100, etc., as contained in the microcontroller 220 or memory 260) to be sent to the external device 254 through an established communication link 266.

The stimulation device 100 can further include one or more physiological sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, where an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 cm$^2$) and/or higher current frequencies (e.g., above about 10 kHz) to reduce noise.

As mentioned, various exemplary techniques include acquiring mechanical information and optionally other information and determining one or more metrics or parameters indicative of cardiac mechanics (e.g., synchrony or dyssynchrony). As described herein, mechanical information can be acquired as position information for an electrode or electrodes with respect to a point or points in time (e.g., times defined in part by a cardiac cycle). Mechanical or position information may, at times, be referred to as motion information.

Figure 3:
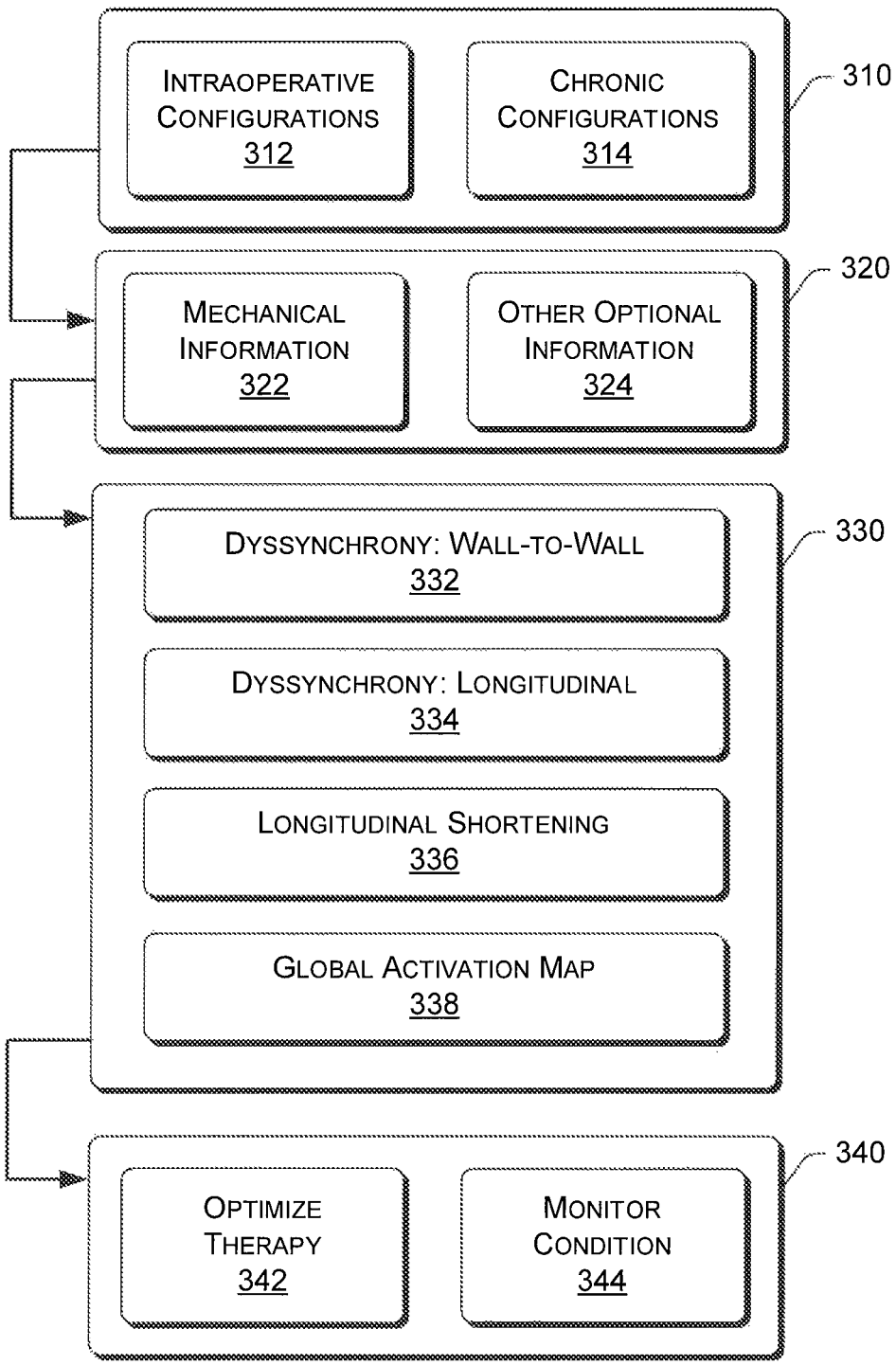
FIG. 3 is a block diagram of an exemplary method for optimizing therapy and/or monitoring conditions based at least in part on mechanical information (e.g., mechanical parameters indicative of dssynchrony).

FIG. 3 shows an exemplary method 300 for acquiring and analyzing mechanical information. In the example of FIG. 3, the method 300 includes a configurations block 310 that includes intraoperative configurations 312 (e.g., acute configurations) and chronic configurations 314. The intraoperative configurations 312 pertain to configurations that may be achieved during an operative procedure. For example, during an operative procedure, one or more leads may be positioned in a patient where the one or more leads are connected to, or variously connectable to, a device configured to acquire information and optionally to deliver electrical energy to the patient (e.g., to the heart, to a nerve, to other tissue, etc.). The chronic configurations 314 pertain to configurations achievable by a chronically implanted device and its associated lead or leads, or more generally, its electrode arrangements. In general, intraoperative configurations include those achievable by physically re-positioning a lead in a patient's body while chronic configurations normally do not allow for re-positioning as a lead or leads are usually anchored during implantation or become anchored in the weeks to months after implantation. Chronic configurations do, however, include selection of a subset of the multiple implanted electrodes, for example using the tip electrode versus the first ring electrode as a cathode or using the tip and first ring as a bipolar pair versus using the tip and ring as two independent cathodes. Thus, intraoperative configurations include configurations available by changing device settings, electrode selection, and physical position of electrodes, while chronic configurations include only those configurations available by changing device settings and electrode selection, or "electronic repositioning" of one or more stimulation electrodes.

As indicated in FIG. 3, an acquisition block 320 includes acquisition of mechanical information 322 and optionally acquisition of other information 324 (e.g., electrical information as to electrical activity of the heart, biosensor information, etc.). While an arrow indicates that a relationship or relationships may exist between the configurations block 310 and the acquisition block 320, acquisition of information may occur by using in part an electrode (or other equipment) that is not part of a configuration. For example, the acquisition block 320 may rely on one or more surface electrodes that define a coordinate system or location system for locating an electrode that defines one or more configurations. For example, three pairs of surface electrodes positioned on a patient may be configured to deliver current and define a three-dimensional space whereby measurement of a potential locates an electrode in the three-dimensional space.

As described herein, an electrode may be configured for delivery of energy to the heart; for acquisition of electrical information; for acquisition of mechanical information; for acquisition of electrical information and mechanical information; for delivery of energy to the heart and for acquisition of electrical information; for delivery of energy to the heart and for acquisition of mechanical information; for delivery of energy to the heart, for acquisition of electrical information and for acquisition of mechanical information.

In various examples, acquisition of mechanical information occurs by measuring one or more potentials where the measuring relies on an electrode that may also be configured to deliver energy to the heart (e.g., electrical energy to pace a chamber of the heart). In such a scenario, the electrode may deliver energy sufficient to stimulate the heart and then be tracked along one or more dimensions to monitor the mechanical consequences of the stimulation. Further, such an electrode may be used to acquire electrical information (e.g., an IEGM that evidences an evoked response). Such an electrode can perform all three of these tasks with proper circuitry and control. For example, after delivery of the energy, the electrode may be configured for acquiring one or more potentials related to location and for acquiring an electrogram. To acquire potentials and an electrogram, circuitry may include gating or other sampling techniques (e.g., to avoid circuitry or interference issues). Such circuitry may rely on one sampling frequency for acquiring potentials for motion tracking and another sampling frequency for acquiring an electrogram.

The method 300 of FIG. 3 includes a determination block 330 for determining one or more parameters such as a wall-to-wall dyssynchrony parameter 332, a longitudinal dyssynchrony parameter 334, a longitudinal shortening parameter 336 and a global activation parameter or map 338.

As shown in the example of FIG. 3, the conclusion block 340 may perform actions such as to optimize therapy 342 and/or to monitor patient and/or device condition 344. These options are described in more detail with respect to FIG. 4.

Figure 4:
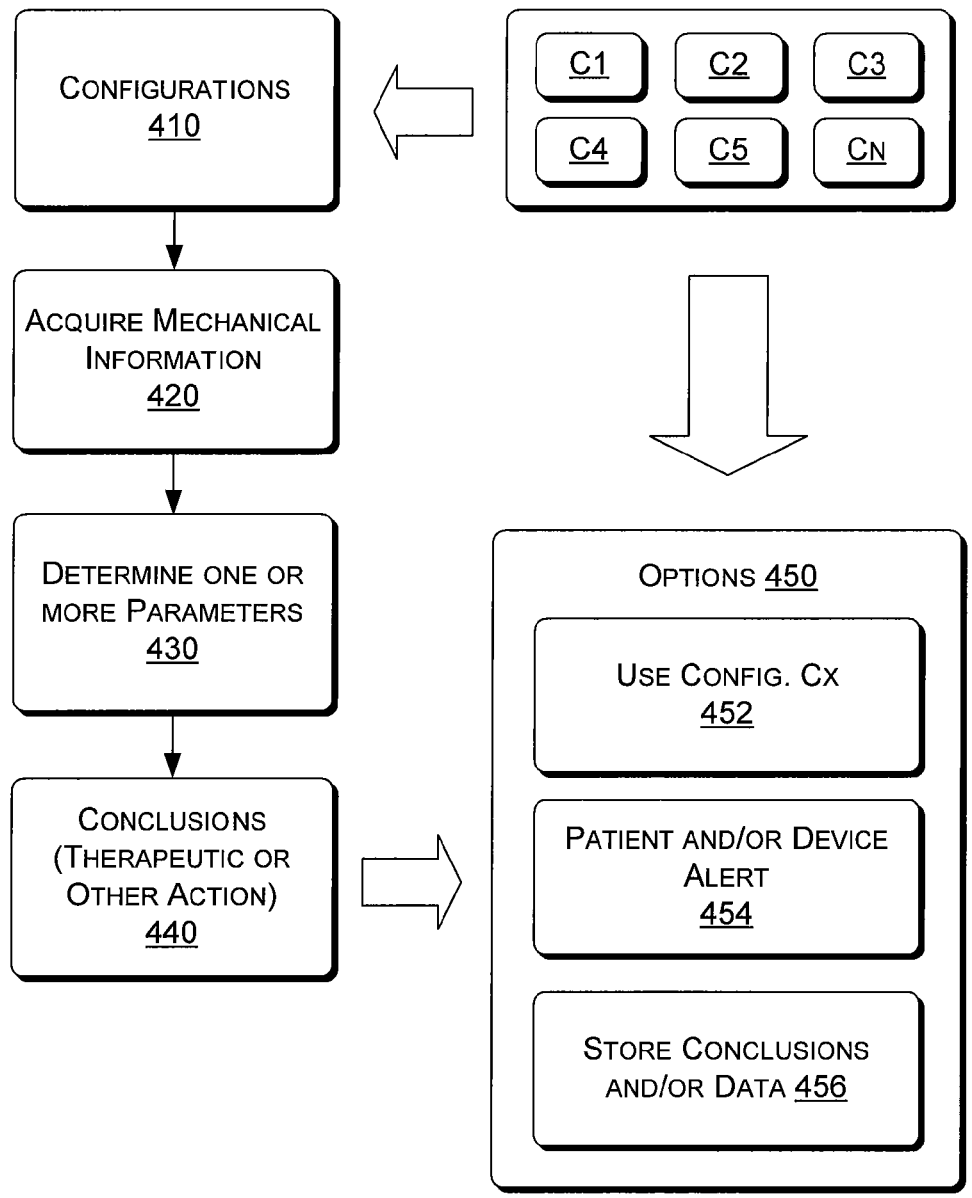
FIG. 4 is a block diagram of the exemplary method of FIG. 3 along with various options.

FIG. 4 shows the exemplary method 400 with various configurations 410 (C1, C2, . . . , Cn) and options 450. As mentioned, a configuration may be defined based on factors such as electrode position (e.g., with respect to some physiological feature of the heart or another electrode), stimulation parameters for an electrode or electrodes and, where appropriate, one or more interelectrode timings. Hence, with reference to FIG. 1, C1 may be a configuration that relies on the RV tip electrode 128, the RV ring electrode 130, the LV tip electrode 122 and the LV ring electrode 124 while C2 may be a configuration that relies on the same electrodes as C1 but where the stimulation polarity for the LV electrodes is reversed. Further, C3 may rely on the same electrodes where the timing between delivery of a stimulus to the RV and delivery of a stimulus to the LV is different compared to C1. Yet further, C4 may rely on the same electrodes where the duration of a stimulus to the RV is different compared to C1. In these foregoing examples, configurations provide for one or more electrodes to deliver energy to stimulate the right ventricle and for one or more electrodes to deliver energy to stimulate the left ventricle. In other examples, configurations may provide for stimulation of a single chamber at one or more sites, stimulation of one chamber at a single site and another chamber at multiple sites, multiple chambers at multiple sites per chamber, etc.

In an acquisition block 420, acquisition occurs for mechanical information where such information pertains to one or more configurations. In a determination block 430, one or more parameters are determined based at least in part on the mechanical information (see, e.g., the parameters of the determination block 330 of FIG. 3). A conclusions block 430 provides for therapeutic or other action, which may be selected from one or more options 450.

In the example of FIG. 4, the one or more options 450 include selection of a configuration 452 (e.g., Cx, where x is a number selected from 1 to n), issuance of a patient and/or device alert 454 that pertains to condition of a patient or a condition of a device or associated lead(s) or electrode(s), and storage of conclusion(s) and/or data 456. The options 450 may be associated with the configurations 410, as indicated by an arrow. For example, storage of conclusions and/or data 456 may also store specific configurations, a generalization of the configurations (e.g., one or more shared characteristics), a device/system arrangement (e.g., where the number and types of configurations would be known based on the arrangement), etc.

As described herein, an exemplary method can include: positioning one or more electrodes within the heart and/or surrounding space (e.g., intra-chamber, intra-vascular, intra-pericardial, etc., which may be collectively referred to as "cardiac space"); and acquiring mechanical information (e.g., via one or more measured potentials) to determine a location, locations or displacement for at least one of the one or more electrodes using an electroanatomic mapping system (e.g., the ENSITE® NAVX® system or other system with appropriate features). In such a method, the positioned electrodes may be configured for acquisition of electrical information (e.g., IEGMs). Further, with respect to acquisition of information, an acquisition system may operate at an appropriate sampling rate. For example, an acquisition system for mechanical information may operate at a sampling rate of about 100 Hz (e.g., the ENSITE® NAVX® system can sample at about 93 Hz) and an acquisition system for electrical information may operate at a sampling rate of about 1200 Hz (e.g., in unipolar, bipolar or other polar arrangement).

As explained, the mechanical information is used to determine one or more parameters (see, e.g., the parameters of the block 330 of FIG. 3). In turn, a therapy may be selected or optimized or condition diagnosed based at least in part on the one or more parameters.

An exemplary method may include preparing a patient for both implant of a device such as the device 100 of FIGS. 1 and 2 and for electroanatomic mapping study. Such preparation may occur in a relatively standard manner for implant prep, and using the ENSITE® NAVX® system or other similar technology for the mapping prep. As described herein, any of a variety of electroanatomic mapping or locating systems that can locate indwelling electrodes in and around the heart may be used.

Once prepped, a clinician or robot may place leads and/or catheters in the patient's body, including any leads to be chronically implanted as part of a CRT system, as well as optional additional electrodes that may yield additional information (e.g., to increase accuracy by providing global information or other information).

After an initial placement of an electrode-bearing catheter or an electrode-bearing lead, a clinician may then connect one or more electrodes to an electroanatomic mapping or locating system. The term "connection" can refer to physical electrical connection or wireless connection (e.g., telemetric, RF, ultrasound, etc.) with the electrodes or wireless connection with another device that is in electrical contact with the electrodes.

Once an appropriate connection or connections have been made, real-time position data for one or more electrodes may be acquired for various configurations or conditions. For example, position data may be acquired during normal sinus rhythm; pacing in one or more chambers; advancing, withdrawing, or moving a location of an electrode; pacing one or more different electrode configurations (e.g. multisite pacing); or varying inter-stimulus timing (e.g. AV delay, VV delay).

In various examples, simultaneous to the position recording, an intracardiac electrogram (IEGM) from each electrode can also be recorded and associated with the anatomic position of the electrode. While various examples refer to simultaneous acquisition, acquisition of electrical information and acquisition of mechanical information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a mapping system recording the real-time motion information at each electrode position in a point-by-point manner. Such motion data can by associated with a respective anatomic point from which it was collected. By moving the electrodes from point to point during an intervention, the motion data from each location can be incorporated into a single map, model, or parameter. As described in more detail below, mechanical information (e.g., motion information) can be used to determine one or more parameters (e.g., one or more of the parameters of the block 330 of FIG. 3).

As explained, an exemplary method may include determining one or more parameters. In turn, an algorithm or a clinician may select a configuration (e.g., electrode location, multisite arrangement, AV/VV timing) that yielded the best value for an electromechanical delay parameter and use the selected configuration as a chronic configuration for the CRT system. Such a chronic configuration may be optionally updated from time to time (e.g., during a follow-up visit, in a patient environment, etc., depending on specific capabilities of a system).

Various exemplary methods, using either a single parameter or a combination of more than one parameter, may automatically select a configuration, present an optimal configuration for acknowledgement by a clinician, or present various configurations to a clinician along with pros and cons of each configuration (e.g., in objective or subjective terms). For example, a particular configuration may be associated with a high power usage that may excessively drain a power source of an implantable device (e.g., device battery 276). Other pros and cons may pertain to patient comfort (e.g., pain, lack of pain, overall feeling, etc.).

An exemplary method may rely on certain equipment at time of implant or exploration and other equipment after implantation of a device to deliver a cardiac therapy. For example, during an intraoperative procedure, wireless communication may not be required; whereas, during a follow-up visit, measured potentials for position of chronically implanted electrodes (e.g., mechanical information) and of measured IEGMs using chronically implanted electrodes (e.g., electrical information) may be communicated wirelessly from an implanted device to an external device. With respect to optimization of a chronically implanted system, in general, electrode location will not be altered, but other parameters altered to result in an optimal configuration (e.g., single- or multi-site arrangement, polarity, stimulation energy, timing parameters, etc.).

As discussed herein, various exemplary techniques deliver current and measure potential where potential varies typically with respect to cardiac mechanics (e.g., due to motion). For example, electrodes for delivery of current may be placed at locations that do not vary significantly with respect to cardiac mechanics while one or more electrodes for measuring potential may be placed at a location or locations that vary with respect to cardiac mechanics. Alternatively, electrodes for measuring potential may be placed at locations that do not vary significantly with respect to cardiac mechanics while one or more electrodes for delivery of current may be placed at a location or locations that vary with respect to cardiac mechanics. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

In accordance with the method 300 of FIG. 3 and the method 400 of FIG. 4, an exemplary method may include preparing a patient for both implant and an electroanatomic mapping study. In this example, preparation can be accomplished in standard manner for implant preparation and the mapping may rely on a localization system such as the ENSITE® NAVX® system or other similar technology for the mapping prep. After preparing the patient, the method includes placing leads and/or catheters in the patient's body, including any leads to be chronically implanted as part of the CRT system, as well as optional additional electrodes that will yield more information, for example, to thereby increase versatility of mechanical dyssynchrony determinations. After placement, the method includes connecting electrodes on leads and/or catheters to the localization system (e.g., electroanatomic mapping system). With respect to the term "connecting", depending on the equipment, it may include physical electrical connecting and/or telemetric/RF/wireless/ultrasound/other communication connecting (e.g., directly or indirectly, via another "bridging" device, with the electrodes.)

After appropriate connections are made, acquiring or recording follows to record real-time positions of one or more electrodes for various configurations or conditions such as, but not limited to: normal sinus rhythm; pacing in one or more chambers (e.g., RV pacing, LV pacing BiV pacing); at various lead placement locations, (i.e., advancing, withdrawing, or moving the location of an electrode); pacing one or more different electrode configurations (e.g. multisite pacing); or varying inter-stimulus timing (e.g. AV delay, VV delay). After or during acquisition, the method can determine one or more mechanical dyssynchrony parameters. Subsequently, based on one or more of the parameters, optionally in conjunction with other information (e.g., other ENSITE® real-time cardiac performance parameters), a clinician or a device may select a configuration (e.g., electrode location, multisite configuration, AV/VV delays, etc.) that yielded or yields the best value(s) for the mechanical dyssynchrony parameter(s). This configuration may then be used chronically (e.g., as the final configuration of the CRT setup).

Such a method may separately be implemented at a clinic or hospital follow-up after the time of implant, provided wireless communication with the chronic indwelling electrodes. In general, it can be assumed that the electrode location will not be altered, but optimization of single- or multi-site configuration as well as timing parameter may still be performed.

As described below in more detail, longitudinal shortening along a RV lead and/or a LV lead can be calculated to estimate long axis function, which may be a good indicator of global ventricular function[1], and therefore provide one or more corresponding parameters for use in optimizing CRT (e.g., during implantation or during follow-up).

[1] A Simpson. "Echocardiographic assessment of long axis function: a simple solution to a complex problem?" Heart 1997; 78:211-212.

Figure 5:
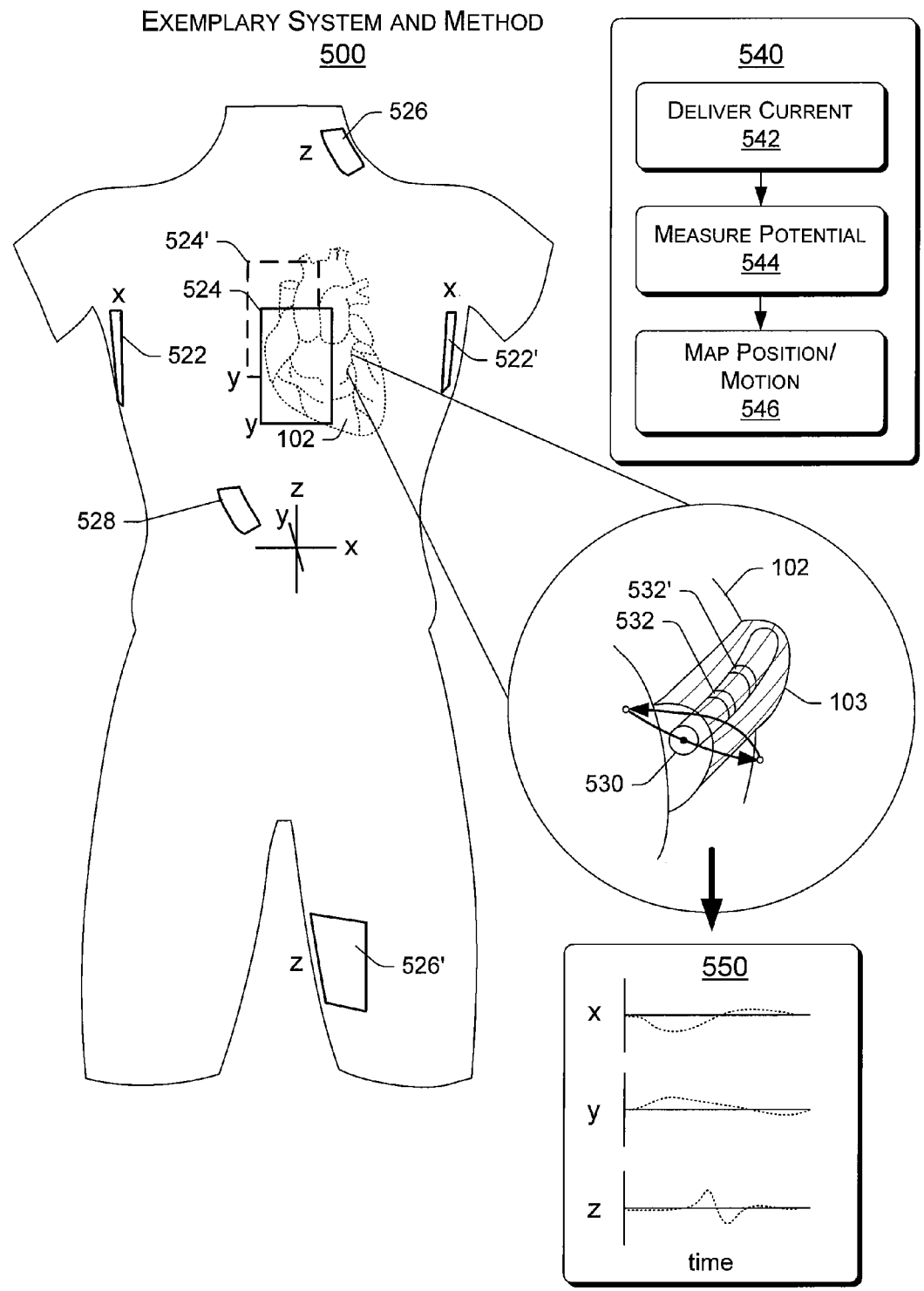
FIG. 5 is an exemplary arrangement of a lead and electrodes for acquiring mechanical information and optionally other information.

FIG. 5 shows an arrangement and method 500 that may rely in part on a commercially available system marketed as ENSITE® NAVX® navigation and visualization system (see also LOCALISA® system, Medtronic, Inc., Minnesota). The ENSITE® NAVX® system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 5, electrodes 532, 532', which may be part of a standard EP catheter 530 (or lead), sense electrical potential associated with current signals transmitted between three pairs of surface electrode patches 522, 522' (x-axis), 524, 524' (y-axis) and 526, 526' (z-axis). An addition electrode patch 528 is available for reference, grounding or other function. The ENSITE® NavX System can also collect electrical data from a catheter and can plot a cardiac electrogram 570 from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NAVX® system may use electrical information to track or navigate movement and construct three-dimensional (3-D) models of a chamber of the heart.

A clinician can use the ENSITE® NAVX® system to create a 3-D model of a chamber in the heart for purposes of treating arrhythmia (e.g., treatment via tissue ablation). To create the 3-D model, the clinician applies surface patches to the body. The ENSITE® NAVX® system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 540, a system (e.g., such as the ENSITE® NavX system) delivers low level separable currents from the three substantially orthogonal electrode pairs (522, 522', 524, 524', 526, 526') positioned on the body surface (delivery block 542) and optionally the electrode 528 (or one or more other electrodes). The specific position of a catheter (or lead) electrode within a chamber of the heart can then be established based on three resulting potentials measured between the recording electrode with respect to a reference electrode, as seen over the distance from each patch set to the recording tip electrode (measurement block 544). Sequential positioning of a catheter (or lead) at multiple sites along the endocardial surface of a specific chamber can establish that chamber's geometry, i.e., position mapping (position/motion mapping block 546). Where the catheter (or lead) 530 moves, the method 540 may also measure motion.

In addition to mapping at specific points, the ENSITE® NAVX® system provides for interpolation (mapping a smooth surface) onto which activation voltages and times can be registered. Around 50 points are required to establish a surface geometry and activation of a chamber at an appropriate resolution. The ENSITE® NAVX® system also permits the simultaneous display of multiple catheter electrode sites, and also reflects real-time motion of both ablation catheters and those positioned elsewhere in the heart.

The ENSITE®D NAVX® system relies on catheters for temporary placement in the body. Various exemplary techniques described herein optionally use one or more electrodes for chronic implantation. Such electrodes may be associated with a lead, an implantable device, or other chronically implantable component. Referring again to FIG. 3, the configuration block 310 indicates that intraoperative configurations 312 and chronic configurations 314 may be available. Intraoperative configurations 312 may rely on a catheter and/or a lead suitable for chronic implantation.

With respect to motion, the exemplary system and method 500 may track motion of an electrode in one or more dimensions. For example, a plot 550 of motion versus time for three dimensions corresponds to motion of one or more electrodes of the catheter (or lead) 530 positioned in a vessel 103 of the heart 102 where the catheter (or lead) 530 includes the one or more electrodes 532, 532'. Two arrows indicate possible motion of the catheter (or lead) 530 where hysteresis may occur over a cardiac cycle. For example, a systolic path may differ from a diastolic path. An exemplary method may analyze hysteresis for any of a variety of purposes including selection of a stimulation site, selection of a sensing site, diagnosis of cardiac condition, etc.

The exemplary method 540, as mentioned, includes the delivery block 542 for delivery of current, the measurement block 544 to measure potential in a field defined by the delivered current and the mapping block 546 to map motion based at least in part on the measured potential. According to such a method, motion during systole and/or diastole may be associated with electrical information. Alone, or in combination with electrical information, the mechanical motion information may be used for selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 500 may use one or more features of the aforementioned ENSITE® NAVX® system. For example, one or more pairs of electrodes (522, 522', 524, 524', 526, 526') may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 532, 532').

The exemplary system 500 may be used to track motion of one or more electrodes due to systolic motion, diastolic motion, respiratory motion, etc. Electrodes may be positioned along the endocardium and/or epicardium during a scouting or mapping process for use in conjunction with electrical information. Such information may also be used alone, or in conjunction with electrical information, for identifying the optimal location of an electrode or electrodes for use in delivering CRT. For example, a location may be selected for optimal stimulation, for optimal sensing, or other purposes (e.g., anchoring ability, etc.).

With respect to stimulation, stimulation may be delivered to control cardiac mechanics (e.g., contraction of a chamber of the heart) and motion information may be acquired where the motion information is associated with the controlled cardiac mechanics. An exemplary selection process may identify the best stimulation site based on factors such as electrical activity, electromechanical delay, extent of motion, synchronicity of motion where motion may be classified as systolic motion or diastolic motion. In general, motion information corresponds to motion of an electrode or electrodes (e.g., endocardial electrodes, epicardial electrodes, etc.) and may be related to motion of the heart.

Figure 6:
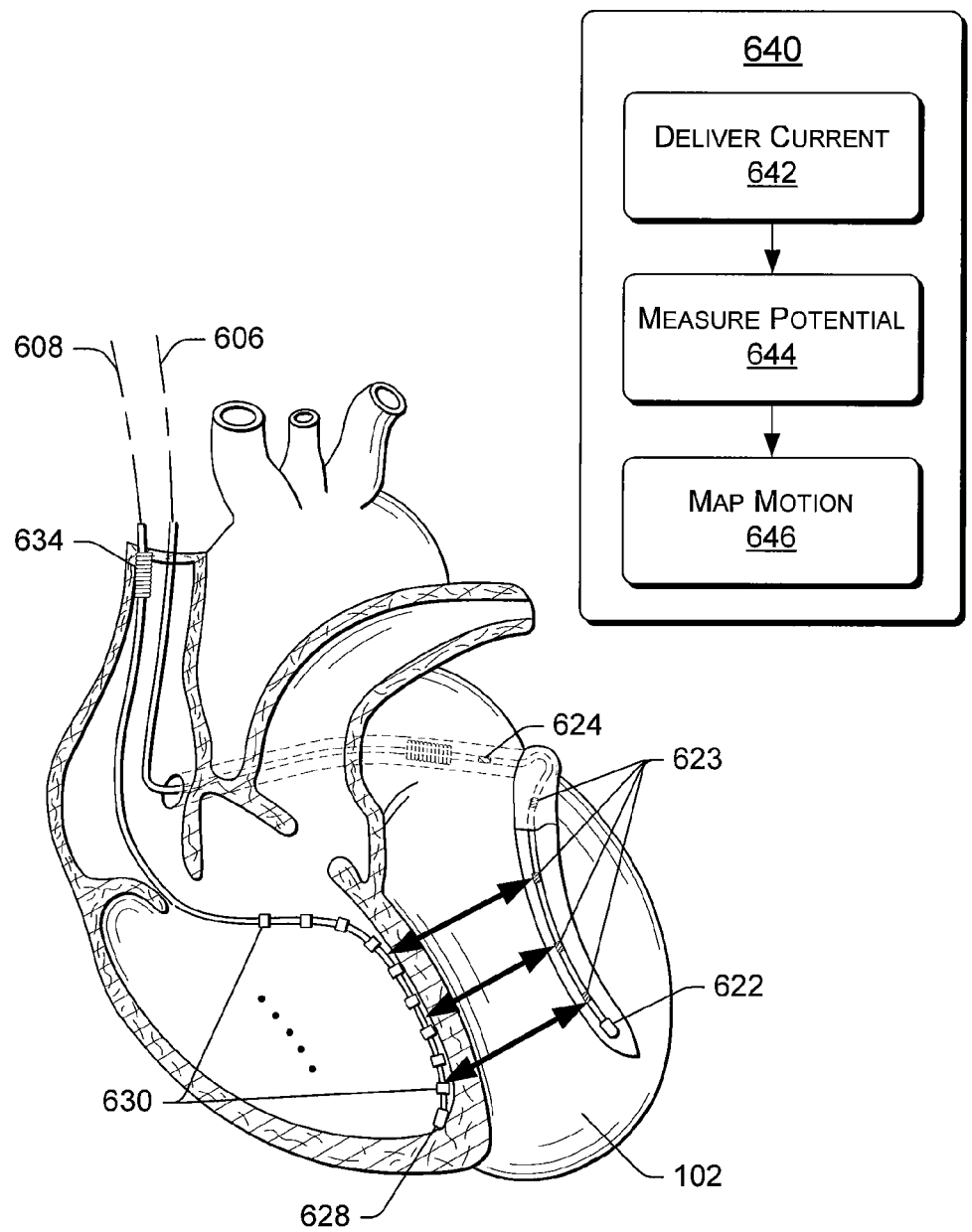
FIG. 6 is a simplified diagram illustrating the heart with right ventricular lead electrodes adjacent a septal wall and left ventricular lead electrodes adjacent a lateral wall along with a block diagram of an exemplary method for mapping lead or electrode motion.

FIG. 6 shows an exemplary arrangement and method 600 that includes two multipolar leads 606, 608 where one lead 606 is position in a vein with at least some electrodes adjacent a lateral wall of the left ventricle of the heart 102 and where the other lead 608 is positioned in the right ventricle of the heart 102 with at least some electrodes adjacent the septal wall that separates the right ventricle and the left ventricle.

In FIG. 6, double headed arrows are shown to indicate movement between these walls of the heart. Such wall-to-wall motion may be estimated using a linear approach or a non-linear approach. For example, given a septal wall point and a lateral wall point at a first time and at a second time, motion may be indicated by the difference between two lines (e.g., a line between the septal wall point and the lateral wall point at the first time and a line between the septal wall point and the lateral wall point at the second time). In this example, the difference between the two lines may be divided by a time difference for the two points in time (e.g., with respect to a cardiac cycle) to determine a wall-to-wall velocity.

The lead 606 includes various features of the lead 106 of FIG. 1. For example, the lead 606 includes a series of ring electrodes 623 along with a tip electrode 622 and a ring electrode 624. As mentioned, the lead 606 includes at least some electrodes positioned adjacent a lateral wall of the left ventricle of the heart 102. Accordingly, these electrodes move with corresponding movement of the lateral wall of the left ventricle.

The lead 608 includes various features of the lead 108 of FIG. 1. For example, the lead 608 includes a tip electrode 828, a series of ring electrodes 630 and a coil electrode 634. In the example of FIG. 6, the lead 608 extends from the SVC through the right atrium and into the right ventricle. The tip electrode 628 is positioned near the apex of the heart 102, which is typically a region that moves less than other regions during contraction. As mentioned, at least some electrodes of the series of ring electrodes 630 are positioned along the septal wall. Accordingly, these electrodes move with corresponding movement of the septal wall.

While a two leads are shown in FIG. 6, other examples may use a single lead or more than two leads. For example, a single lead may include a bifurcation to two or more branches that allow for placement of electrodes adjacent the septal wall and for placement of electrodes adjacent the lateral wall of the left ventricle. In another example, a single lead may be positioned in the right ventricle with electrodes adjacent the septal wall and then repositioned in a vein with electrodes adjacent the lateral wall of the left ventricle. In such a manner, information may be acquired for both septal motion and lateral wall motion, while not simultaneously, at different times where markers or other techniques can align or otherwise relate septal wall motion and lateral wall motion with respect to a portion or portions of a cardiac cycle. In yet other examples, a basket type lead may be used with splines that may extend to an interior wall of chamber of the heart. Such splines may include one or more electrodes for use in acquiring cardiac motion information.

The electrodes 623, 630 may be used according to an exemplary method 640. For example, in a delivery block 642, current may be delivered to a region of the heart that includes at least some of the series of electrodes 623, at least some of the series of electrodes 630 or a combination of one or more of the series of electrodes 623 and one or more of the series of electrodes 630. In a measurement block 644, one or more of the electrodes 623, 630 may be used to measure potential or potentials associated with the delivered current. Such potential or potentials may be measured at a particular point in time or at more than one point in time. A mapping block 646 then uses the potential or potentials to map motion of the heart (e.g., the septal wall, the lateral wall or a combination of the septal wall and the lateral wall).

With respect to delivery of current per the delivery block 642, surface patches may be used (e.g., 522, 522', 524, 524', 526, 526' of FIG. 5) or, for example, implanted electrodes (e.g., electrodes of FIG. 1 or those of FIG. 6).

As already described, various exemplary techniques may be used to acquire motion information (e.g., spatially for 1-D, 2-D or 3-D and generally with respect to time). In general, acquisition of motion information relies on current delivery and potential measurement. Electrodes may be positioned in the body and/or external to the body. Electrodes may be positioned within the pericardial space, as defined by the pericardium (e.g., in a vessel/chamber of the heart, etc.), and/or outside the pericardial space (e.g., consider the case electrode of the device 100 of FIGS. 1 and 2 or the surface patch electrodes of the system 500 of FIG. 5). Electrodes may be positioned at the pericardium, at the epicardial surface of the heart or between the pericardium and the epicardial surface of the heart. Electrodes may be implanted chronically or temporarily. Electrodes may optionally be suitable for stimulating the heart (e.g., pacing, shocking, etc.).

An exemplary method includes positioning an implantable lead in a chamber of the heart where the lead includes a series of electrodes and where at least some of the electrodes contact a wall of a chamber of the heart, delivering current, measuring potentials, associated with the current, using the electrodes that contact the wall of the chamber and mapping motion of the wall based at least in part on the measured potentials. Such a method may include delivering current using one or more electrodes positioned on the skin of the patient and/or one or more implanted electrodes. Such a method may deliver current to generate at least a one-dimensional coordinate system. In the foregoing method, the wall may be the septal wall between the right ventricle and the left ventricle or it may be a free wall of the right ventricle or a free wall of the left ventricle (e.g., lateral wall). Mapped motion of a chamber wall may be used for selecting one or more parameters of a bi-ventricular pacing therapy.

Figure 7:
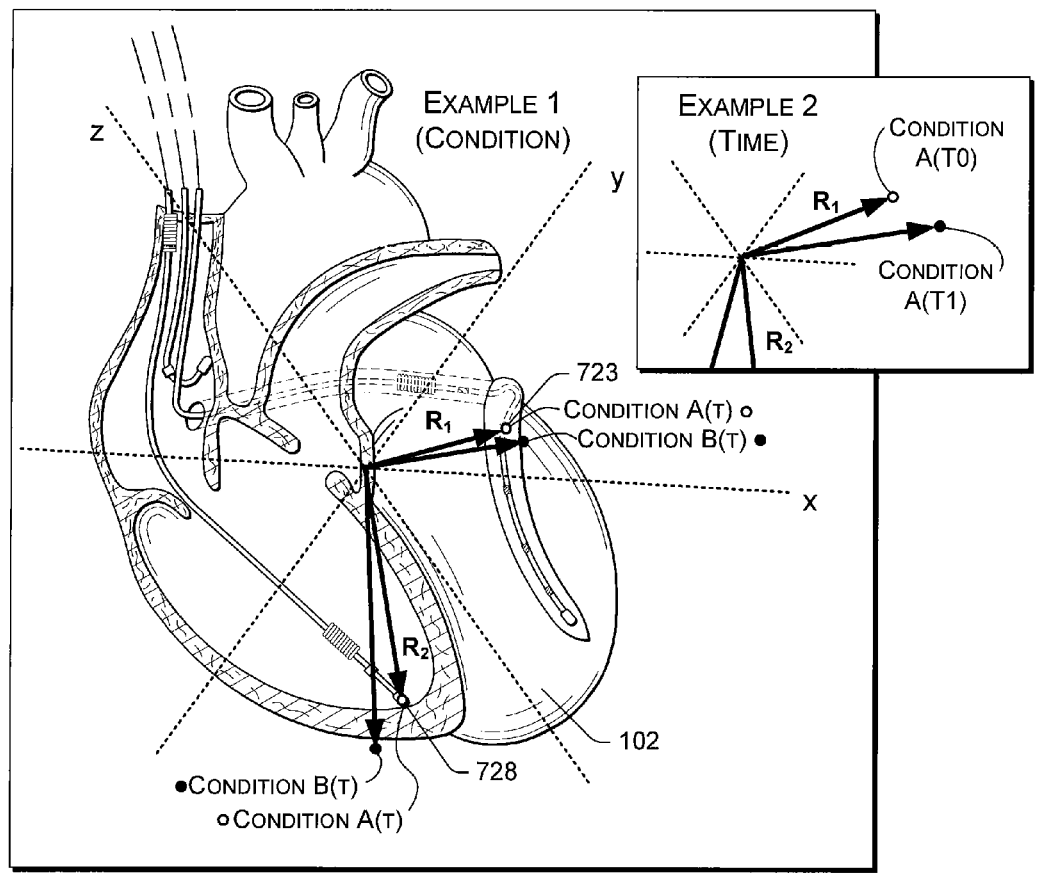
FIG. 7 is a simplified diagram illustrating the heart with respect to electrodes and a coordinate system whereby positions of electrodes may be indentified using vectors, for example, to compare motion for different conditions (e.g., A and B) or times in a cardiac cycle (e.g., T0 and T1).

FIG. 7 shows another exemplary arrangement and method 700. FIG. 7 includes a "condition" example (Example 1) and a "time" example (Example 2) where synchrony determinations may be made with respect to two conditions (e.g., pacing on and off) or with respect to time (e.g., just before peak systole and at peak systole). A diagram of the heart 102 includes a coordinate system that allows for defining vectors $\vec{R}_1$ and $\vec{R}_2$ with respect to electrodes 723 and 728, respectively. In the exemplary method of FIG. 7, movement of any electrode may be related to an origin. In absence of a coordinate system, a fiducial marker, another electrode or the like may provide guidance. For example, the apex of the heart is known to exhibit less movement than some other regions. As such, an electrode positioned at or near the apex of the right ventricle may serve as a marker for analyzing movement of one or more other electrodes. As an alternative, movement of various electrodes may be tracked and an origin inferred (e.g., by averaging or other techniques).

Referring again to the coordinate system of FIG. 7, the coordinate system may be established, at least in part, by assessing potentials associated with currents applied to a patient's body. For example, as the heart cycles, potentials may be averaged to filter out motion of the heart and the potentials analyzed to determine an origin for a coordinate system that corresponds to the current delivery system. Further, once the origin that corresponds to the current delivery system has been determined, it may be offset wholly or in part according to some aspect of the heart, such as, the geometry of the heart and, in particular, a major axis of the left ventricle. Accordingly, vectors may be determined based on an origin set in association with a current delivery system or otherwise set.

In FIG. 7, two $\vec{R}_1$ vectors are shown for an electrode 723 on a lateral wall of the left ventricle and two $\vec{R}_2$ vectors are shown for an electrode 728 in the right ventricle. The vectors are shown in a 3-D coordinate system with a stationary origin. In Example 1, the vectors are presented for two different conditions: condition A and condition B. Specifically, for Example 1, the vectors are presented where condition A pertains to no pacing and where condition B pertains to pacing where open circles correspond to condition A and where filled circles correspond to condition B. In contrast, for Example 2, the vectors are presented for a single condition and for two times during a cardiac cycle. Specifically, for Example 2, the vectors are presented for condition A (no pacing) and for times T0 (peak systole minus some small time δ) and T1 (peak systole) where open circles correspond to T0 and where filled circles correspond to T1.

Given the vectors, it is possible to determine yet another pair of vectors for $\vec{R}_1$ and $\vec{R}_2$ that represent the direction and magnitude of the difference for $\vec{R}_1$ and for $\vec{R}_2$ given conditions A and B at a particular time (Example 1) or given two times T0 and T1 for a particular condition (Example 2).

As mentioned, in FIG. 7, the vectors $\vec{R}_1$ and $\vec{R}_2$ correspond to the positions of the electrodes 723 and 728, respectively. Again, in Example 1, the vectors $\vec{R}_1$ and $\vec{R}_2$ correspond to no pacing at peak systole (condition A) and pacing at peak systole (condition B) while in Example 2, the vectors $\vec{R}_1$ and $\vec{R}_2$ correspond to condition A at time T0 and condition A at time T1. Mathematically, the position of electrode 723 $P_1(t_p)$ and the position of electrode 728 $P_2(t_p)$ can be expressed by vectors $\vec{R}_1$ and $\vec{R}_2$, which are described as a function of position coordinate (x, y, z) and time $t_p$ as follows:

$$P_1(t_p) = \vec{R}_1(x_1, y_1, z_2, t_p)$$

$$P_2(t_p) = \vec{R}_2(x_2, y_2, z_2, t_p)$$

For Example 1, the direction and magnitude difference, in vector notation, may be represented as $\Delta \vec{R}_{1,t} = \vec{R}_{1A,t} - \vec{R}_{1B,t}$, which is the displacement for electrode 723 during pacing or CRT off (A) and on (B), and $\Delta \vec{R}_{2,t} = \vec{R}_{2A,t} - \vec{R}_{2B,t}$, which is the displacement for electrode 728 during pacing or CRT off (A) and on (B). While specific conditions A and B are given, one or more other pacing interventions may represent a base or a test condition (pacing sites, AV & VV timings, pacing configurations).

For Example 2, the direction and magnitude difference, in vector notation, may be represented as $\Delta \vec{R}_1 = \vec{R}_{1,T0} - \vec{R}_{1,T1}$, which is the displacement for electrode 723 between time T0 and time T1 and $\Delta \vec{R}_2 = \vec{R}_{2,T0} - \vec{R}_{2,T1}$, which is the displacement for electrode 728 between time T0 and time T1.

Optimization of a therapy may rely on examining conditions as in Example 1, examining times in a cardiac cycle as in Example 2 or a combination of conditions and times. As described herein optimization of a pacing therapy (e.g., CRT) may occur according to one or more of the following exemplary approaches:

(1) Collecting $\Delta \vec{R}_1 \cdot \Delta \vec{R}_2$ at about five or more time points in a cardiac cycle, particularly during systole for CRT optimization and if more than about 50% or more of sample points exhibit $\Delta \vec{R}_1 \cdot \Delta \vec{R}_2 < 0$; then the heart is synchronized and the electrode configuration or pacing scheme is acceptable. In this approach, if $(|\Delta \vec{R}_1| + \Delta \vec{R}_2|) \rightarrow MAX$, then CRT may be considered optimized. In other words, if the sum of movement at the sites is large with a negative dot product (e.g., between sites or groups of sites), effective pumping may be inferred. For example, consider the arrangement of FIG. 7, for the given positions of electrodes 723 and 728, a negative dot product indicates that the electrodes 723 and 728 are moving in opposite directions or towards one another. As these electrodes are on opposing walls of the left ventricle, left ventricular function can be characterized. If various conditions are examined and one of those conditions results in the sum of the magnitudes being a maximum and the dot product negative, then that condition may be considered optimal. The condition may pertain to a lead placement, a pacing parameter, etc. Where times are analyzed over a cardiac cycle, it is possible to determine the extent of synchrony over portions of a cardiac cycle. This approach may analyze times over a cardiac cycle for one condition and then analyze times over a cardiac cycle for another condition. Dot product analysis for each condition can provide synchrony measures for each condition, which can then be compared.

(2) Using a dot product, the second approach determines if $\Delta \vec{R}_1 \cdot \Delta \vec{R}_2 > 0$ during both diastole and systole. If this criterion is met, then the heart is desynchronized. For example, if one of the vectors corresponds to a LV electrode site, then one may conclude that the LV site is not satisfactory or the patient is a non-responder.

(3) In the third approach, if $\Delta \vec{R}_1 = 0$ and $\Delta \vec{R}_2 = 0$, where the conditions are for no CRT (A) and CRT (B), then the heart is not responding to CRT. Given such a result, a clinician may consider implanting LV lead in a different branch, or concluding that the patient is a non-responder.

In an alternative formulation, a CRT outcome can be defined by relative electrode motion behavior between a first electrode and a second electrode. For example, the change of motion can be described as follows:

$$\tau = \frac{\Delta \vec{R}_1 - \Delta \vec{R}_2}{\Delta \vec{R}_1}$$

Provided with this equation, CRT may be considered optimized when τ is maximized.

Figure 8:
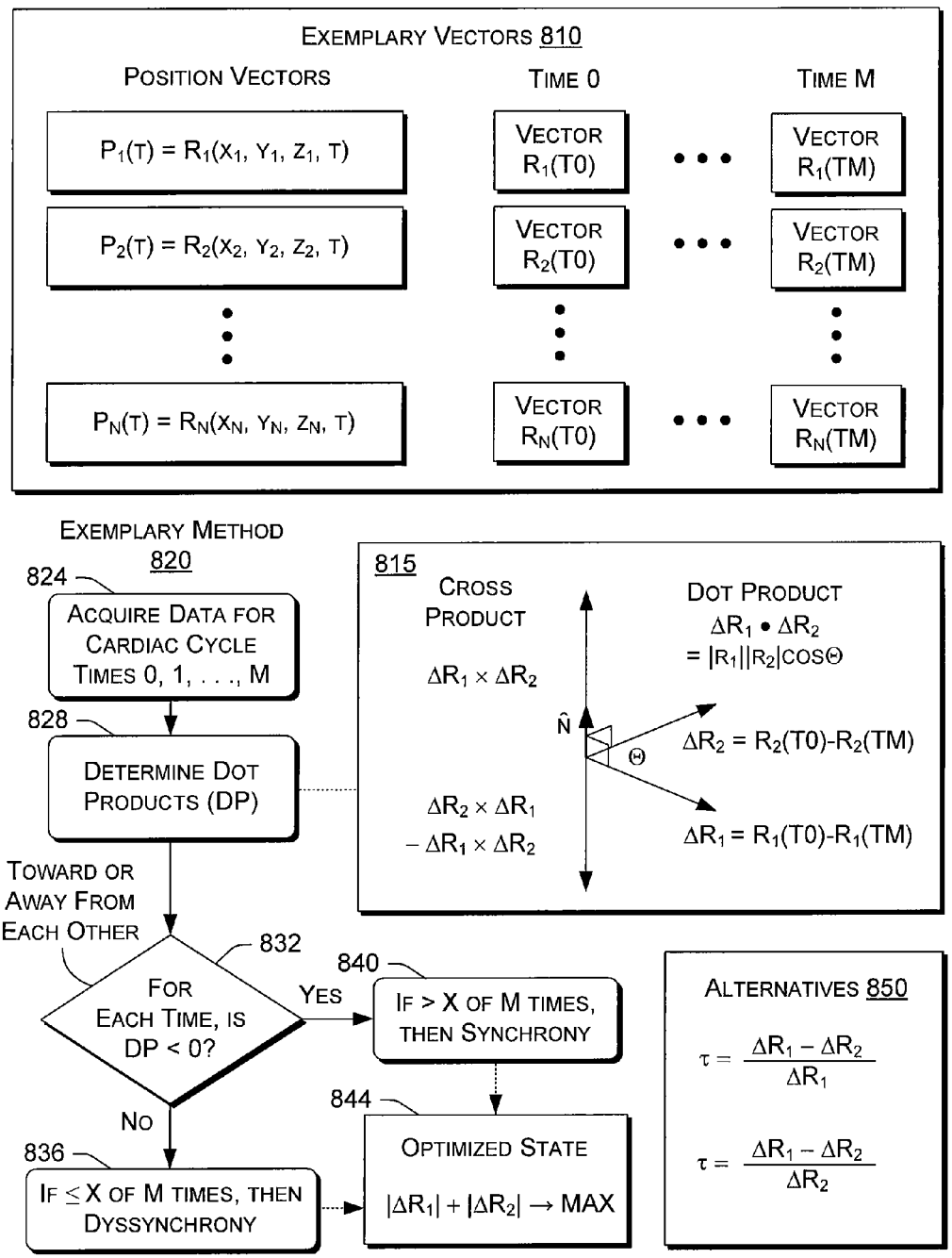
FIG. 8 is a block diagram of various vectors and vector operations along with an exemplary method that relies on one or more vector operations.

FIG. 8 shows exemplary vectors 810 and an exemplary method 820 that relies on vectors, which corresponds to the technique of Example 2 of FIG. 7 where multiple times may be considered. The vectors 810 include position vectors defined in a Cartesian coordinate system and for multiple times from T0 to TM. The times T0 to TM correspond to times in a cardiac cycle and may be acquired subject to a condition, which may correspond to any of a variety of conditions including electrode configuration (e.g., site), pacing therapy parameters, drug administration, respiration (holding breath, inhalation, exhalation), etc. As respiration is associated with respiratory sinus arrhythmia (RSA) and autonomic tone, such a comparison may provide insight into autonomic function of a patient. As described herein, where respiration gives rise to motion artifacts, a respiration compensation scheme may be applied to filter out motion or position artifacts caused by respiration to thereby provide more accurate data as to cardiac motion.

In FIG. 8, the exemplary method 820 commences in an acquisition block 824 that acquires data for cardiac cycle times 1, 2, . . . , M, for a patient. For example, one of the cardiac cycle times may be an end diastolic time and another cardiac cycle time may be an end systolic time. In this example, data would be acquired for at least two electrodes at these times. Further, positions with respect to the times for an electrode may be plotted to show a path traversed by the electrode during a cardiac cycle. Path information for one or more electrodes may be relied on to augment a vector analysis.

In a determination block 828, the method 820 determines at least a dot product for at least two vector differentials that are based on the acquired data. For example, a diagram shows the dot product and the cross product of the vectors differentials $\Delta \vec{R}_1$ and $\Delta \vec{R}_2$. The dot product is a scaler that may be calculated in various manners (e.g., as indicated in block 815 of FIG. 8). Other vector operations may be applied such as a vector cross product operation, which provides additional information that may assist in optimization of a pacing therapy or diagnosis of a cardiac condition.

After determination of the dot product, the method 820 enters a decision block 832 that decides if the dot product (DP) for each of the times is less than zero, which indicates that the movement differentials are either moving away from each other or toward each other. During a cardiac cycle, such synchronized movement during systole and diastole can indicate that the heart function is adequate. As shown in the example of FIG. 8, if the decision block 832 decides that, for one of the times, the dot product is less than zero, then the method 820 enters a determination block 840 that determines if the dot products for more than X of the M times are less than zero, the heart motion is synchronized by the particular condition. In this example, X may be one half of M (e.g., 50%) or some other corresponding percentage where if the criterion is met, a clinician can be assured that the heart is moving in a synchronized manner. However, if the decision block 832 decides that the dot product is not less than zero, then the method 820 enters a determination block 836 that determines, if the dot products for a less than (or equal to) X of the M times are greater than zero, the heart is dyssynchronized by the particular condition (e.g., CRT using a certain unsuitable electrode configuration).

In either instance of the decision block 832, the method 820 may further proceed to an optimization block 844 that determines whether a condition (e.g., an electrode configuration, a pacing therapy scheme, a drug, etc.) is optimal. The optimization block 844 may also trigger an optimization algorithm that aims to adjust one or more of the conditions and to return to the acquisition block 824 of the method 820. For example, if a test condition delivers CRT using unipolar pacing of the left ventricle, the optimization block 844 may adjust the CRT to use bi-polar pacing of the left ventricle and ultimately compare the magnitude of the differential vectors for the two conditions or to a base condition (e.g., no CRT).

As described herein, the method 820 may be performed multiple times where upon a first run data are acquired for a particular condition. In a subsequent run, data may be acquired for a different condition. Vector analysis may rely on data for both runs to compare conditions at specific times and performance of the conditions over an entire cardiac cycle. Regarding the latter, a first condition may result in 9 of 15 cardiac cycle times having a dot product less than zero (60%) while a second condition may result in 13 of 15 cardiac cycle times having a dot product less than zero (87%). Based on this analysis, an algorithm may conclude that the second condition exhibits greater synchrony.

FIG. 8 also shows two alternative approaches 850 for formulating a vector based metric. In these alternative approaches 850 CRT may be considered optimized when X is maximized. The alternative approaches 850 rely on a normalized magnitude differential. A dot product approach may be combined with a normalized magnitude differential approach to assess a condition or conditions (e.g., decide whether one condition results in more synchronous contraction, optimize a therapy, etc.).

Figure 9:
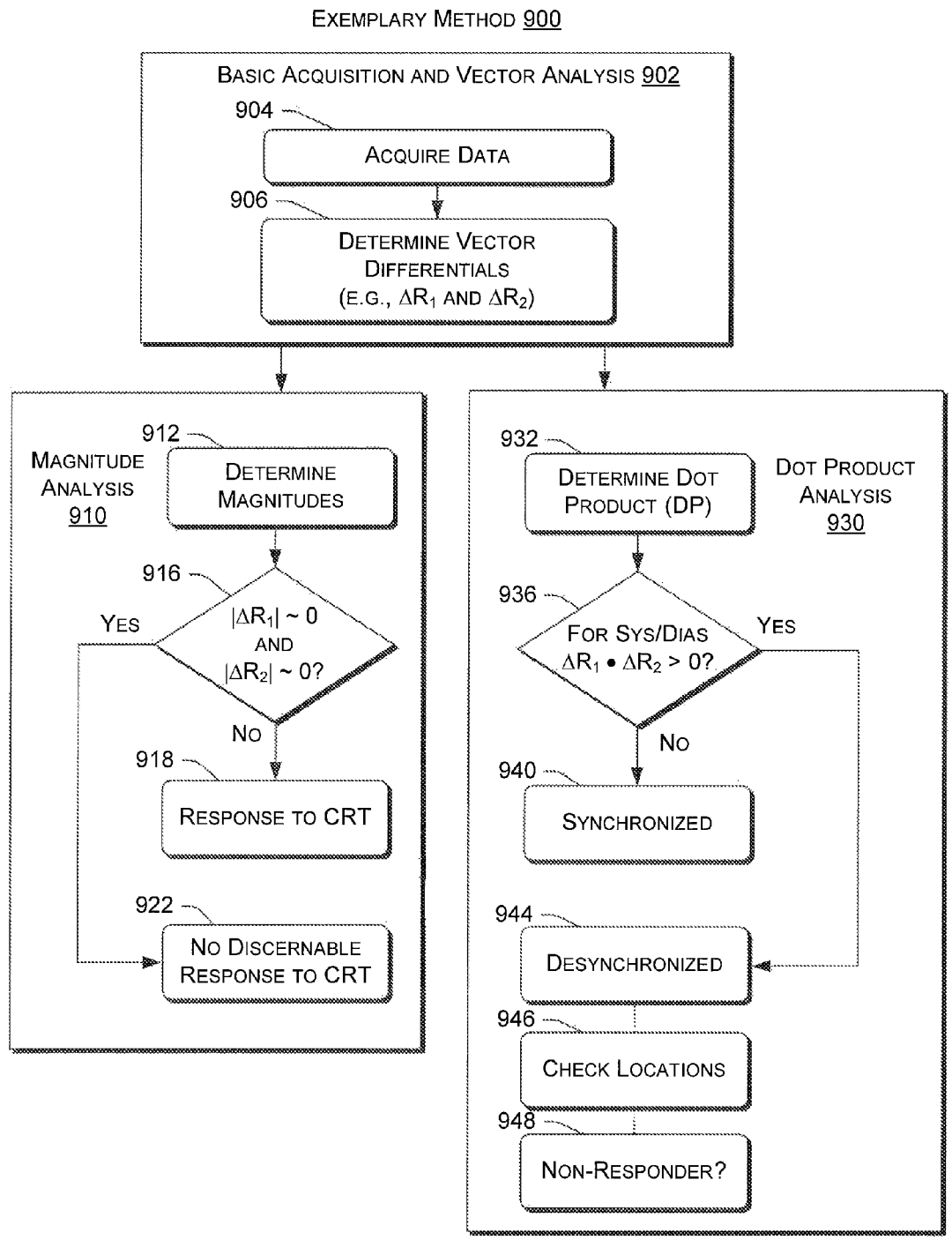
FIG. 9 is a block diagram of an exemplary method that can determine whether synchrony exists or whether a patient is likely to respond to CRT.

FIG. 9 shows an exemplary method 900 for vector-based assessments of cardiac synchrony. Specifically, the method 900 relies on an acquisition and basic vector analysis 902 followed by vector magnitude analysis 910 and/or vector dot product analysis 930. The method 900 commences in a data acquisition block 904 that acquires position data for two or more electrodes with respect to two or more points in time as associated with a cardiac cycle (see, e.g., Example 2 of FIG. 7 and FIG. 8). A determination block 906 follows that determines vector differentials based on the acquired data. As explained with respect to Example 2 of FIG. 7 and FIG. 8, a vector differential represents direction and magnitude of electrode position for two points in time. In the determination block 906, vector differentials are determined for two or more electrodes. In general, the location of each of the electrodes is known, for example, as being along a lateral wall, a septal wall, apex of the right ventricle, etc. Location information can aid in analyses by providing, a priori, an indication as to how two electrodes should move with respect to each other during a cardiac cycle or during administration of a stimulus or shock. In the example of FIG. 9, after the basic acquisition and vector analysis 902, the method 900 may proceed to the magnitude analysis 910 and/or the dot product analysis 930.

The magnitude analysis 910 includes a magnitude determination block 912 that determines the magnitude for each of the vector differentials. A decision block 916 follows that decides whether each of two or more magnitude values is approximately zero. When a magnitude value for an electrode is approximately zero, it is inferred that the electrode and its surrounding or corresponding myocardium did not move to any significant degree between a first time and a second time. When multiple electrodes do not move to any significant degree, then it may be inferred that one or more corresponding regions of the heart did not move significantly between a first time and a second time. Where CRT is an applied condition, lack of movement (i.e., magnitude values approximately zero) indicates that CRT is ineffective and that the patient is likely a non-responder to CRT. Hence, if the decision block 916 decides that the magnitude values are not approximately zero, a response to CRT block 918 follows, which may suitably notify a clinician. In contrast, if the decision block 916 decides that the magnitude values are approximately zero, a non-response block 922 follows, which may suitably notify a clinician that no discernable response occurred to upon delivery of CRT. As described in more detail with respect to FIG. 19, the method 900 may be implemented using a computing device such as a device programmer. Such a computing device may be configured to allow a clinician to select one or more vector analyses and to display results, including the notifications of the blocks 918 and 922.

Referring to the dot product analysis 930, a determination block 932 determines a dot product based on the vector differentials of block 906. A decision block 936 follows that decides whether the dot product for two vector differentials is greater than zero during systole and whether the dot product for two vector differentials is greater than zero during diastole. As mentioned, a dot product less than zero infers synchrony and, correspondingly, a dot product greater than zero infers dyssynchrony. Thus, if the decision block 936 decides that the dot products are not greater than zero, a synchronized notification block 940 follows; whereas, if the decision block 936 decides that the dot products are greater than zero, a desynchronized notification block 944 follows, which may further call for checking electrode locations 946 or determining whether the patient is a non-responder to CRT 948. As described in more detail with respect to FIG. 19, the method 900 may be implemented using a computing device such as a device programmer. Such a computing device may be configured to allow a clinician to select one or more vector analyses and to display results, including the notifications of the blocks 940 and 944 (e.g., and the blocks 946, 948 or other suitable actions).

As described herein, the method 820 of FIG. 8 and the method 900 of FIG. 9 may be applied where electrodes are positioned with respect to opposing walls of a ventricle of the heart to assess wall-to-wall dyssynchrony. The mechanical dyssynchrony between two opposing left ventricular walls can give valuable information on global left ventricular function. In particular, the dyssynchrony between the septal wall and a free left ventricular wall is of interest because the mechanical delay between two such walls can be theoretically the longest.

In an exemplary method, CRT outcome is defined by wall motion for two or more locations on a heart. In various examples, electrodes are placed at LV lateral wall (e.g., the electrode 723 of FIG. 7) and RV apex (e.g., the electrode 728 of FIG. 7); noting that, in general, electrode positions might be anywhere on heart; either intra-ventricular or inter-ventricular. In such an exemplary method, cardiac motion data of the LV lateral wall electrode and the RV apex electrode may be acquired for a CRT off condition and a CRT on condition. As mentioned, a reference point for motion determinations may be an electrode on the body or in the heart which is relatively stable and independent with respect to pacing electrode(s) (e.g., ENSITE® belly patch, defibrillation patch, lollipop, electrode on other EP catheters or electrode on the delivery tool, etc.); noting that other techniques for providing an origin to establish a coordinate system may be used.

As described in Example 1 of FIG. 8, an exemplary method can perform a vector analysis to compare conditions. Such a method can include providing a first implanted electrode implanted along a lateral wall of the left ventricle; providing a second implanted electrode implanted along a septal wall between the right ventricle and the left ventricle; for a first condition, for a time in a cardiac cycle, determining a three-dimensional position of the first implanted electrode and a three-dimensional position of the second implanted electrode; for a second condition, for the time in a cardiac cycle, determining a three-dimensional position of the first implanted electrode and a three-dimensional position of the second implanted electrode; determining a first vector differential based on a vector for the first implanted electrode for the first condition and another vector for the first implanted electrode for the second condition; determining a second vector differential based on a vector for the second implanted electrode for the first condition and another vector for the second implanted electrode for the second condition; deciding whether the dot product of the first vector differential and the second vector differential is less than zero, and, if the dot product is less than zero, determining that one of the conditions causes the first electrode and the second electrode to either move toward each other or away from each other when compared to the other of the conditions.

Such a method may include deciding whether the first vector differential and the second vector differential are approximately zero; and, if the first vector differential and the second vector differential are approximately zero, determining that the first condition and the second condition do not affect cardiac synchrony. Additionally or alternatively, such method may include determining the magnitude of the first vector differential and the magnitude of the second vector differential, summing the magnitudes and deciding whether the sum of the magnitudes is greater than a previously determined sum of magnitudes for the first implanted electrode and the second implanted electrode at the time in the cardiac cycle.

As described in Example 2 of FIG. 8, an exemplary method can perform a vector analysis to compare times. Such a method can include providing a first implanted electrode implanted along a lateral wall of the left ventricle; providing a second implanted electrode implanted along a septal wall between the right ventricle and the left ventricle; for a time in a cardiac cycle, determining a three-dimensional position of the first implanted electrode and a three-dimensional position of the second implanted electrode; for another time in a cardiac cycle, determining a three-dimensional position of the first implanted electrode and a three-dimensional position of the second implanted electrode; determining a first vector differential based on a vector for the first implanted electrode for the time in the cardiac cycle and another vector for the first implanted electrode for the other time in the cardiac cycle; determining a second vector differential based on a vector for the second implanted electrode for the time in the cardiac cycle and another vector for the second implanted electrode for the other time in the cardiac cycle; deciding whether the dot product of the first vector differential and the second vector differential is less than zero; and, if the dot product is less than zero, determining that the first electrode and the second electrode to either move toward each other or away from each other.

As described with respect to FIG. 9, a method can include a dot product analysis (see, e.g., 930). Such a method can include various steps of the foregoing method (see Example 2 of FIG. 8) where the times in the cardiac cycle include times during systole and further include repeating the method for times during diastole and deciding whether the dot product is greater than zero for the times during systole and whether the dot product is greater than zero for the times during diastole; and, if the dot product is greater than zero for the times during systole and for the times during diastole, the method can include determining that the motion of the first electrode and the second electrode indicates dyssynchrony of cardiac motion.

As described with respect to FIG. 9, a method can include a dot product analysis (see, e.g., 910). Such a method can include various steps of the foregoing method (see Example 2 of FIG. 8) and include deciding whether the first vector differential and the second vector differential are approximately zero; and, if the first vector differential and the second vector differential are approximately zero, the method can include determining that a condition applied to the heart does not effect cardiac synchrony. Such a method can also consider conditions applied to the heart such as application of cardiac resynchronization therapy (CRT). Additionally or alternatively, a method can include determining the magnitude of the first vector differential and the magnitude of the second vector differential, summing the magnitudes and deciding whether the sum of the magnitudes is greater than a previously determined sum of magnitudes for the first implanted electrode and the second implanted electrode at the times in the cardiac cycle.

One of the foregoing dot product methods can include, for the time in a cardiac cycle, determining, over multiple cardiac cycles, a three-dimensional position of the first implanted electrode and a three-dimensional position of the second implanted electrode where the position of the first implanted electrode at the time includes or is an average of multiple positions and where the position of the second implanted electrode at the time includes or is an average of multiple positions. A foregoing dot product method may include, for the other time in a cardiac cycle, determining, over multiple cardiac cycles, a three-dimensional position of the first implanted electrode and a three-dimensional position of the second implanted electrode where the position of the first implanted electrode at the other time includes or is an average of multiple positions and where the position of the second implanted electrode at the other time includes or is an average of multiple positions. Various methods can optionally be performed for more than two times in a cardiac cycle.

Wall-to-Wall Dyssynchrony

Figure 10:
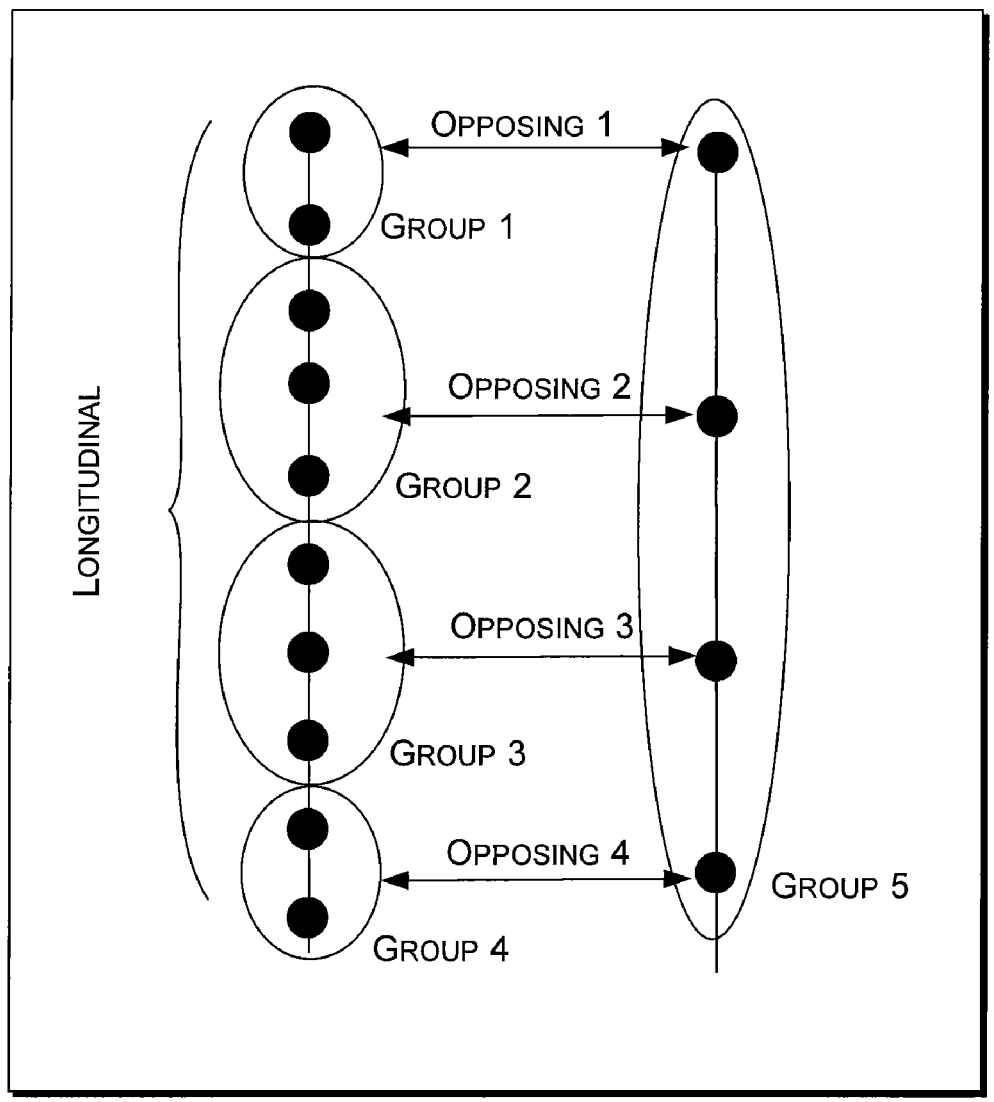
FIG. 10 is a diagram illustrating various manners by which electrodes may be grouped for purposes of determining one or more mechanical dyssynchrony parameters.

FIG. 10 shows a diagram of an exemplary wall-to-wall scheme 1000. According to the scheme 1000, differences in time-to-peak displacement can be computed between opposing electrodes. In FIG. 10, five groups of electrodes are shown, for example, with electrode groups 1 to 4 associated with one lead and electrode group 5 associated with another lead. Given such an arrangement, group 1 can be compared to an opposing group 5; labels "Opposing 1" to "Opposing 4" indicate such electrode comparisons.

Given the scheme 1000, an analysis can preserve the sign (±) of a difference value to determine direction of a mechanical activation pattern. For example, if group 2 is a septal wall group and group 5 is a LV lateral wall group and the corresponding measured septal wall-to-LV lateral wall mechanical delay is less than zero (i.e., a negative value), this indicates that the direction of contractile propagation starts at group 2 of the septal wall and ends with group 5 of the LV lateral wall.

The computed mechanical delays can be averages over multiple heart beats (e.g., cardiac cycles) within each localization system recorded segment (e.g., different lead location, pacing configuration, etc). In turn, beat-averaged mechanical delays can be averaged over all of the electrode pairings on a set of opposing leads/catheters, thus covering the longitudinal span of the myocardium.

In a particular clinical trial, septal-to-lateral wall dyssynchrony and acute hemodynamics (as assessed by change in pressure with respect to time, dP/dt) were determined. Data from this clinical trial are shown in FIGS. 11, 12, 13 and 14. In an exemplary method, times to peak displacements of multiple electrodes on a respective lead/catheter can be averaged. Accordingly, the difference between two averaged times to peak displacements provides a wall-to-wall dyssynchrony metric. Such an approach can also be formulated to ensure that all motion from the longitudinal span of the lead/catheter is incorporated into the final parameter.

FIG. 11 shows a plot of septal wall information 1110 along with acquired data 1120 upon which the septal wall information 1110 is based. The acquired data 1120 corresponds to data acquired using a distal tip electrode on a RV apical lead during RV-only pacing. The plot 1120 includes an ECG, an IEGM and a position with respect to time track over a course of about 7000 ms (e.g., about 13 cardiac cycles). In the plot 1110, an ECG for a single cardiac cycle includes a filled triangle that marks a Q wave onset time and a position track for the same cardiac cycle includes a filled triangle that marks a peak position time. As shown, for the septal wall, the difference between these two times is the time to peak position during the cardiac cycle, which is referred to as $\Delta t_p$.

FIG. 12 shows a plot of LV lateral wall information 1210 along with acquired data 1220 upon which the LV lateral wall information 1210 is based. The acquired data 1220 corresponds to data acquired using a distal tip electrode on a catheter in a lateral branch vein of the left ventricle during RV-only pacing. The plot 1220 includes an ECG, an IEGM and a position with respect to time track over a course of about 7000 ms (e.g., about 13 cardiac cycles). In the plot 1210, an ECG for a single cardiac cycle includes a filled triangle that marks a Q wave onset time and a position track for the same cardiac cycle includes a filled triangle that marks a peak position time. As shown, for the lateral wall, the difference between these two times is the time to peak position during the cardiac cycle, which is referred to as $\Delta t_p$.

Figure 13:
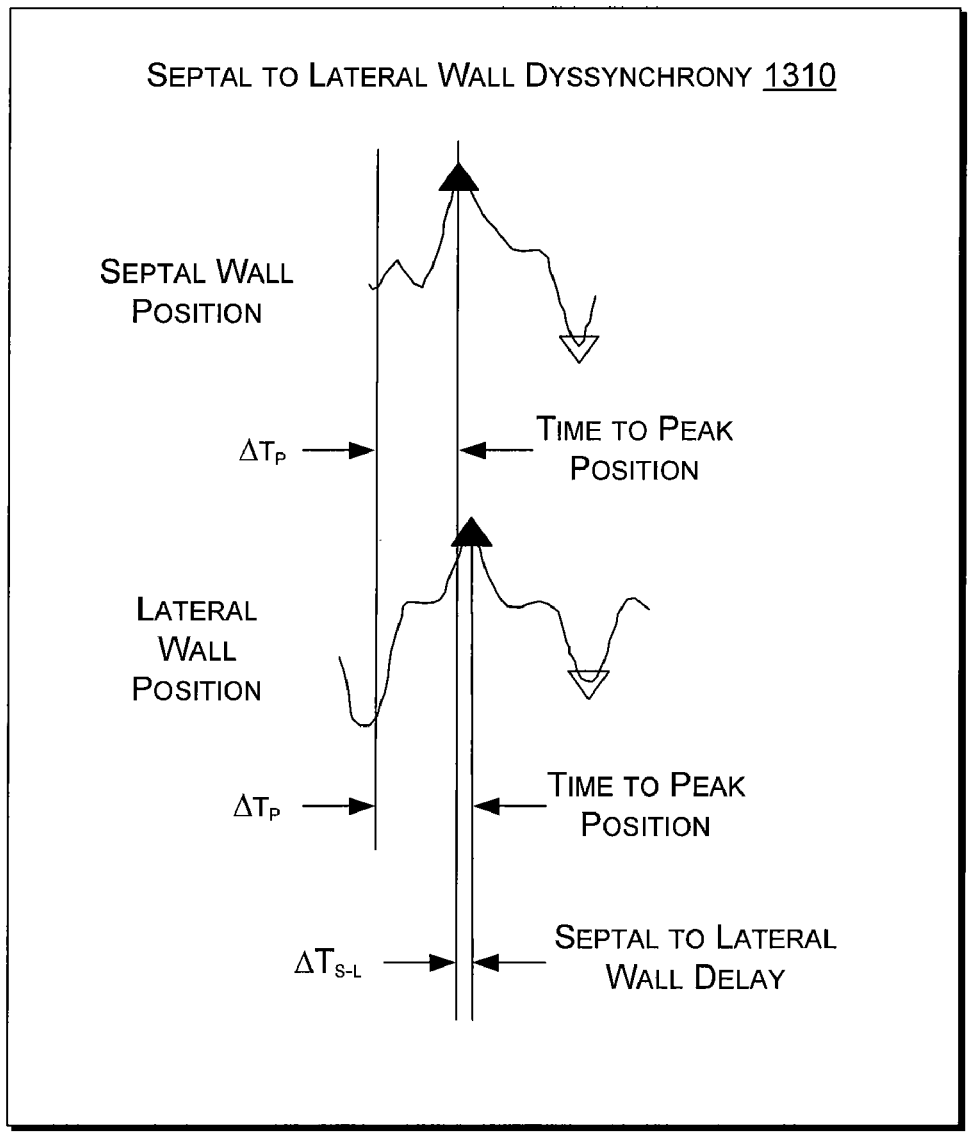
FIG. 13 is a plot of septal wall information and lateral wall information sufficient to determine a septal to lateral wall delay parameter representative of ventricular synchrony or dyssynchrony.

FIG. 13 shows a plot 1310 of septal wall information and lateral wall information sufficient to calculate a septal-to-lateral wall dyssynchrony measure. Specifically, the plot 1310 shows the difference between $\Delta t_p$ of the septal wall and $\Delta t_p$ of the lateral wall as a measure of septal wall to lateral wall delay, which is indicative of septal-to-lateral wall dyssynchrony and, in general, ventricular dyssynchrony.

Figure 14:
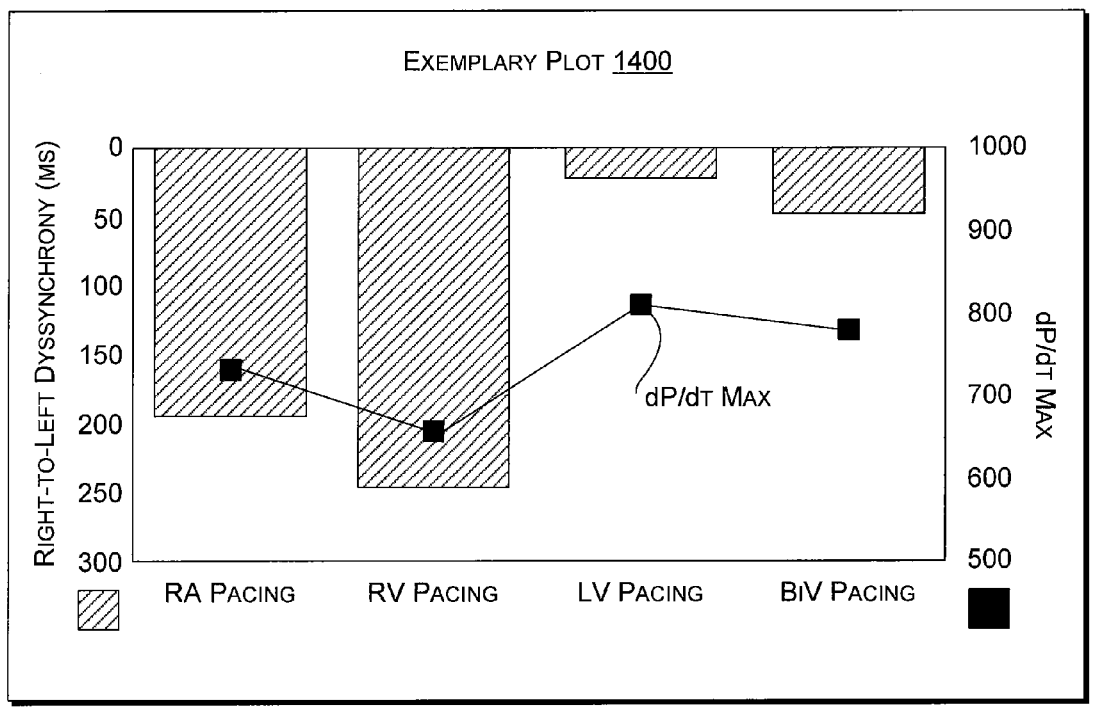
FIG. 14 is a plot of two dyssynchrony metrics for various pacing conditions.

FIG. 14 shows a plot 1400 of trial data for right atrial pacing (RA pacing), right ventricular pacing (RV pacing), left ventricular pacing (LV pacing) and biventricular pacing (BiV pacing). The plot 1400 provides bars that correspond to right-to-left dyssynchrony in milliseconds (ms) on an inverted scale and filled squares that correspond to maximum pressure (change in pressure with respect to time). Pressure is an accepted hemodynamic measure for assessing cardiac performance and, in particular, the maximum change in pressure with respect to time (dP/dt). Pressure change with respect to time is shown in FIG. 14 to demonstrate that the exemplary right-to-left dyssynchrony measure correlates with an accepted standard invasive pressure measure. For the plot 1400, LV pressure data were acquired using a Millar pressure sensor (e.g., Ultra-Miniature MIKRO-TIP®, Millar Instruments, Inc., Tex.).

As demonstrated by the data of the plot 1400, the RV pacing condition produced the greatest right-to-left dyssynchrony and the lowest maximum LV pressure change for a cardiac cycle (i.e., worst condition); whereas, the LV pacing condition produced the smallest right-to-left dyssynchrony and the highest maximum LV pressure change for a cardiac cycle (i.e., best condition). The results also indicate that the tested biventricular pacing condition performs quite similarly to the tested LV pacing condition. The approach described with respect to FIGS. 11 to 14 may be augmented via a vector analysis (see, e.g., FIGS. 7 to 9).

FIG. 15 shows a plot 1510 of septal-to-lateral wall delay versus time and subject to an exemplary method 1520. As shown in FIG. 15, during a data acquisition period, an acquisition block 1524 of the method 1520 acquires information to determine a septal-to-lateral wall delay or delays for a patient. If the method 1520 decides that the delay or delays are unacceptable (e.g., outside of an acceptable bound or bounds), then the method 1520 calls an optimization block 1528 to optimize the septal-to-lateral wall motion. As indicated in the plot 1510, the optimization routine adjusts one or more parameters associated with a cardiac pacing therapy to minimize the septal-to-lateral wall delay. Such a routine may operate according to any of a variety of general optimization routines, whether single variable or multi-variable. Further, the routine may consider one or more factors other than septal-to-lateral wall delay. For example, a constraint may be placed on pacing energy expended by a cardiac pacing therapy, the number of site where pacing energy is delivered, etc. As indicated in the plot 1510, the optimization block 1528 acts to diminish the septal-to-lateral wall delay to less than a predetermined positive limit and a predetermined negative limit (e.g., as indicated by the dashed lines in the plot 1510). Upon completion of the optimization, the method 1520 enters a pacing block 1532 that delivers the pacing therapy as optimized. The method 1520 may run periodically, upon a trigger or other instruction. Where the method 1520 runs post-operatively, as mentioned, it is unlikely that lead position will be an adjustable variable for purposes of optimization. Hence, optimization will normally rely on selectable electrode configurations, timings and other adjustable parameters associated with a cardiac pacing therapy. If the method 1520 runs in an intraoperatively, then it may be possible, if necessary, to adjust electrode position as part of an optimization process.

As described herein, tracking electrodes in the intracardiac, intravascular, or intrapericardial space over the course of one or more cardiac cycles can provide an estimate or estimates of myocardial motion. In turn, such estimate(s) can be used to derive one or more mechanical dyssynchrony parameters. Where conditions consider CRT or no CRT, the one or more mechanical dyssynchrony parameters can help decide if a patient is a responder, likely to be a responder or is not a responder. Further, for those patients where beneficial response to CRT is demonstrated or otherwise likely, the one or more mechanical dyssynchrony parameters may be used to optimize delivery of CRT. For example, such parameters can be used in the optimization of pacing lead location, electrode configuration, AV/VV delays, etc.

As described herein, an exemplary method can include, for a cardiac cycle, determining a septal to lateral wall time delay as a difference between a time of a peak three-dimensional position of an electrode located along the lateral wall and a time of a peak three-dimensional position of an electrode located along the septal wall; determining a peak velocity for at least one of the electrodes; and adjusting a cardiac pacing therapy to minimize the time delay and to maximize the peak velocity. Such a method can include determining a peak velocity for both of the electrodes. With respect to the adjusting, such a method can optionally adjust a cardiac pacing therapy from performing single ventricle pacing to performing biventricular pacing.

As described herein, an exemplary method can include providing a feature time corresponding to appearance of a feature of electrical activity during a cardiac cycle; providing a time, during the cardiac cycle, corresponding to a peak three-dimensional position of an electrode located along a septal wall between the right ventricle and the left ventricle; providing a time, during the cardiac cycle, corresponding to a peak three-dimensional position of an electrode located along a lateral wall of the left ventricle; for the cardiac cycle, with respect to the feature time, determining a septal to lateral wall time delay as a difference between the time of the peak position of the electrode located along the lateral wall and the time of the peak position of the electrode located along the septal wall; and based on the difference, deciding whether, during the cardiac cycle, cardiac motion was dyssynchronous. Such a method can include repeating the providings (i.e., the providing steps) and the determining for multiple cardiac cycles. Various methods can additionally include, if the deciding decides that the cardiac motion was dyssynchronous during the cardiac cycle, calling for delivery of a cardiac pacing therapy.

In various methods, a cardiac cycle can be an intrinsic cardiac cycle or a paced cardiac cycle associated with a cardiac pacing therapy. Further, if a method decides that the cardiac motion was dyssynchronous during the cardiac cycle, it may call for optimization of the cardiac pacing therapy. For example, an optimization may optimize the cardiac pacing therapy by reducing the septal to lateral wall time delay.

Longitudinal Dyssynchrony

As mentioned, a particular approach can discern longitudinal dyssynchrony. For example, an exemplary method may acquire data using a right ventricular lead (or catheter) and a left ventricular lead (or catheter) and determine one or more longitudinal dyssynchrony metrics based on the acquired data. With reference to FIG. 10, an exemplary method, can group a proximal (basal) electrode with a distal (apical) electrode on the same lead/catheter. In general, a multipolar lead/catheter that has a distance between a distal electrode and a proximal electrode that spans the length of the chamber will provide a better representation of longitudinal dyssynchrony. In contrast, a standard bipolar lead will yield a limited longitudinal dyssynchrony value that represents only a certain region of the myocardial space.

According to the aforementioned method, differences in time-to-peak displacement are computed between one or more electrode groups and optionally opposing electrodes. In such a comparison, the sign (±) of the computed difference value can be preserved to determine direction of a mechanical activation pattern. For example, if a measured base-to-apex mechanical delay provides a negative value, then this indicates that the direction of contractile propagation starts at the base and ends with the apex.

In the aforementioned method, the computed mechanical delays can be averages over multiple cardiac cycles within a localization system recorded segment (i.e., different lead location, pacing configuration, etc). In turn, the beat-averaged longitudinal mechanical delays for the RV lead and the LV lead can averaged over both leads thereby covering the wall-to-wall span of the myocardium.

Global Dyssynchrony

As described herein, one or more global dyssynchrony metrics may be determined based on acquired position information with respect to time. For example, mechanical delays between isoplanar electrodes on adjacent leads/catheters in the intrapericardial space of the LV may be computed, yielding a global activation map of dyssynchrony.

Figure 16:
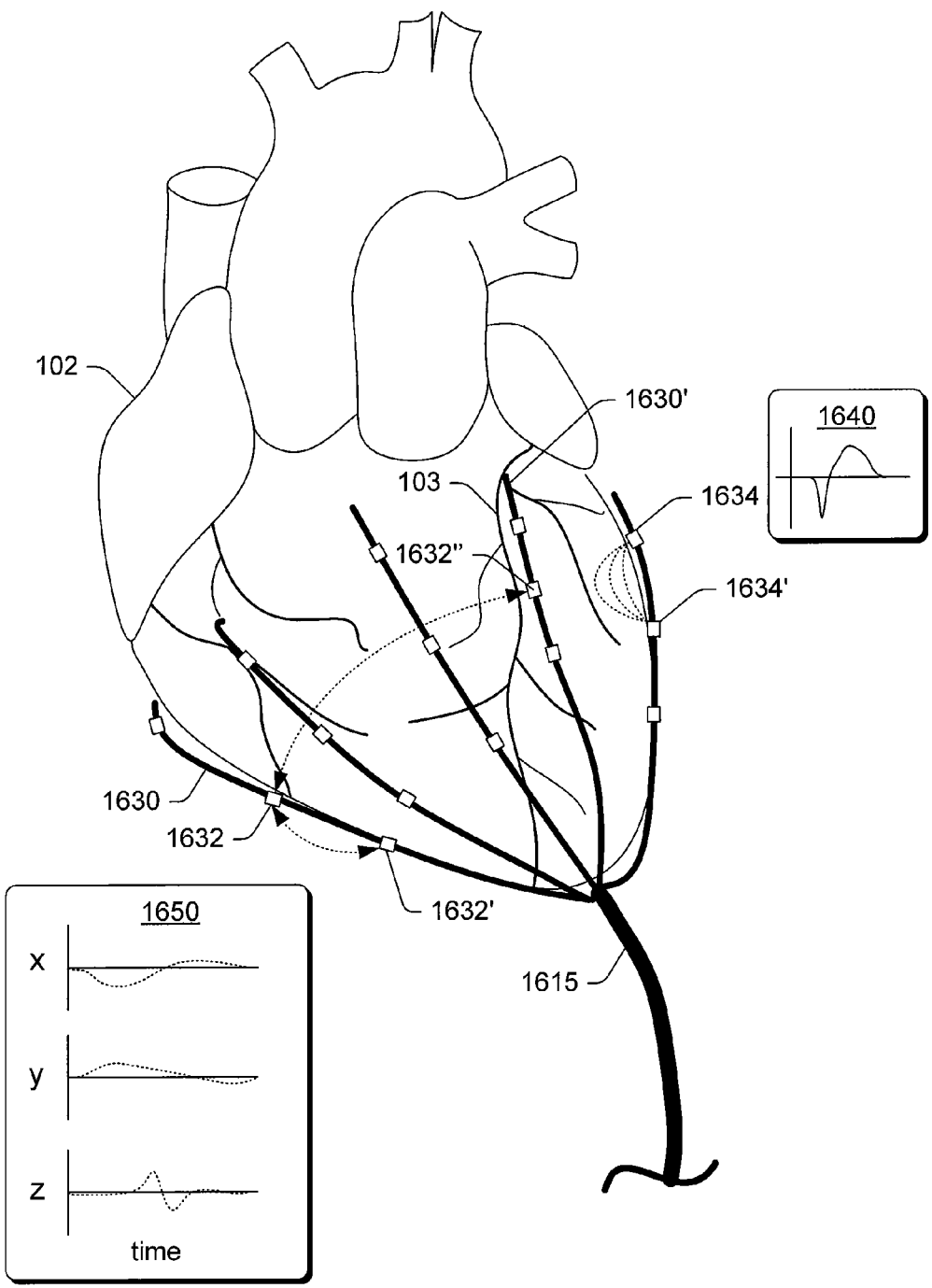
FIG. 16 is a diagram of an exemplary catheter for use in an exemplary global dyssynchrony method that determines one or more global dyssynchrony parameters.

FIG. 16 shows an exemplary catheter 1600 for use in acquiring motion information 1650 (e.g., plot of potential versus time as measured using two or more electrodes). The catheter 1600 includes a main branch 1615 that branches into a plurality of splines 1630, 1630' where each spline may include one or more electrodes 1632, 1632', 1632", 1634, 1634'. Noting that not all splines or electrodes include reference numerals in FIG. 16. Further, while not shown in FIG. 16, the catheter 1600 includes one or more connectors to electrically connect the various electrodes to an acquisition device or system (e.g., a computer-based data acquisition system). The catheter 1600 may operate in conjunction with one or more other electrodes not shown in FIG. 16. For example, the main branch 1615 may include a reference electrode and/or one or more surface electrodes may be used. The catheter 1600 may be used in conjunction with the system and method of FIG. 5 where, for example, current is introduced using surface electrodes 522, 522', 524, 524', 526 and 526'.

While the example of FIG. 16 refers to a catheter, in an alternative system, the catheter 1600 may be a lead configured for chronic implantation in the body and with appropriate features for electrical connection to an implantable device. In yet another alternative, the lead includes appropriate electronics and a power supply disposed along one or more sections of the lead. In this latter example, a separate implantable device may not be required.

The basket-like catheter 1600 (or alternative lead) may be introduced into the body via any of a variety of procedures. For example, such a catheter may be positioned using subxyphoid access to the pericardium. Such a technique may use fluoroscopic guidance. A retractable sheath may be used to expose splines or splines may extend out of a sheath. The splines may have some resiliency such that the splines fit snugly to the myocardial surface. The splines may include one or more anchoring mechanisms to help anchor the splines. Such mechanisms may be extendable and/or retractable. In general, such mechanisms avoid risk of rupture to cardiac arteries. Fluoroscopic or other guidance may be used to minimize risk of injury to one or more cardiac arteries.

While anterior splines are shown in FIG. 16, the catheter 1600 may include posterior splines as well. The splines 1630, 1630' of the catheter 1600 are capable of surrounding a portion of the ventricles. The splines 1630 may be positioned across one or more vessels such as cardiac veins 103. Such veins 103 may be of sufficient size to allow for placement of an electrode via the coronary sinus or other venous access. In general, for purposes of CRT, an electrode may be positioned via a vessel or via pericardial access.

As already mentioned, the catheter 1600 may be used in conjunction with one or more patch electrodes positioned on the surface of a patient's body. In such an arrangement, various electrodes of the catheter 1600 may be used to measure potential or to deliver current and various patch electrodes may be used to deliver current or to measure current (see, e.g., system and method 500 of FIG. 5). For example, the patch electrodes may deliver current while the catheter electrodes measure potential. Referring to FIG. 16, cardiac mechanics will cause movement of the splines 1630 and associated electrodes 1632, 1632', 1632", 1634, 1634'. In turn, the measured potential will vary as a function of cardiac mechanics.

Potential may be measured across any of the electrodes of the catheter 1600. For example, potential may be measured between the electrode 1632 and the electrode 1632' (e.g., same spline) or between the electrode 1632 and the electrode 1632" (e.g., different splines). Accordingly, using a catheter with multiple electrodes positioned in the pericardial space, a variety of measurements may be made to understand better cardiac mechanics.

While the catheter 1600 may be used for acquiring motion information, one or more of the electrodes 1632, 1632', 1632", 1634, 1634' may be used to deliver stimulation energy to the myocardium. For example, the electrodes 1634, 1634' may be used to deliver stimulation energy to the left ventricle (e.g., lateral wall of left ventricle) at a time and level sufficient to cause an evoked response 1640. After delivery of stimulation energy, either or both of the electrodes 1634, 1634' may be used to measure potential over time, which, in turn, may be used to determine motion of the lateral wall of the left ventricle when stimulated at a stimulation site defined by the electrodes 1634, 1634'. Cardiac electrical activity information 1640 may be used in conjunction with motion information 1650 for any of a variety of purposes.

Various studies indicate that fat pads or neural plexuses exist on the epicardial surface. Where a therapy includes delivery of energy to a nerve (e.g. a fat pad, an autonomic nerve, neural plexus, etc.), then the catheter 1600 may be used to help identify an appropriate stimulation site or delivery of energy to such a site may occur in conjunction with acquisition of motion information. Another catheter, lead, electrode, etc., may be used to deliver energy to a nerve where the catheter 1600 acquires motion information, for example, as a function of such energy delivery. Further, a clinician may administer a drug, a maneuver (Valsalva maneuver, tilt test, etc.), etc., that could affect cardiac mechanics where the catheter 1600 is used to acquire motion information as a function of such action.

An exemplary catheter includes a sheath, a plurality of splines extending from the sheath and configured to conform to the heart, a plurality of electrodes disposed on various splines and a connector to connect the electrodes to a measuring device to measure potentials using the electrodes. Such a catheter may include current delivery electrodes and a connector to connect the current delivery electrodes to a current delivery device. In such an example, the measuring device measures potentials associated with the current delivered by the current delivery electrodes. Further, the measuring device and the current delivery device may be the same device.

In an exemplary method to determine one or more global dyssynchrony metric, a patient may have a basket catheter (e.g., the catheter 1600 of FIG. 16 or an interchamber basket catheter such as the CONSTELLATION® catheter marketed by Boston Scientific, Natick, Mass. with a modified open end), which has multiple splines spanning the circumference of the chamber, placed in the intrapericardial space, over at least a portion of the heart (e.g., including a portion of the LV chamber). Such a catheter may include splines that are compliant and deform with the contraction and relaxation of the heart during a cardiac cycle to thereby capture motion of the myocardium. In such an approach, mechanical delays between each adjacent electrode-to-electrode pair can be calculated across various splines and for various longitudinal levels (e.g., from base to apex). The accumulation of these mechanical delays can produce a global activation metric or map. Such a global metric or map can provide a clinician, during an intraoperative phase, with a comprehensive understanding or view of dyssynchrony occurring (e.g., LV dyssynchrony). While two basket types of catheters have been mentioned, alternatively, a balloon catheter having multiple splines may be inserted into LV chamber via retrograde aortic access.

Figure 17:
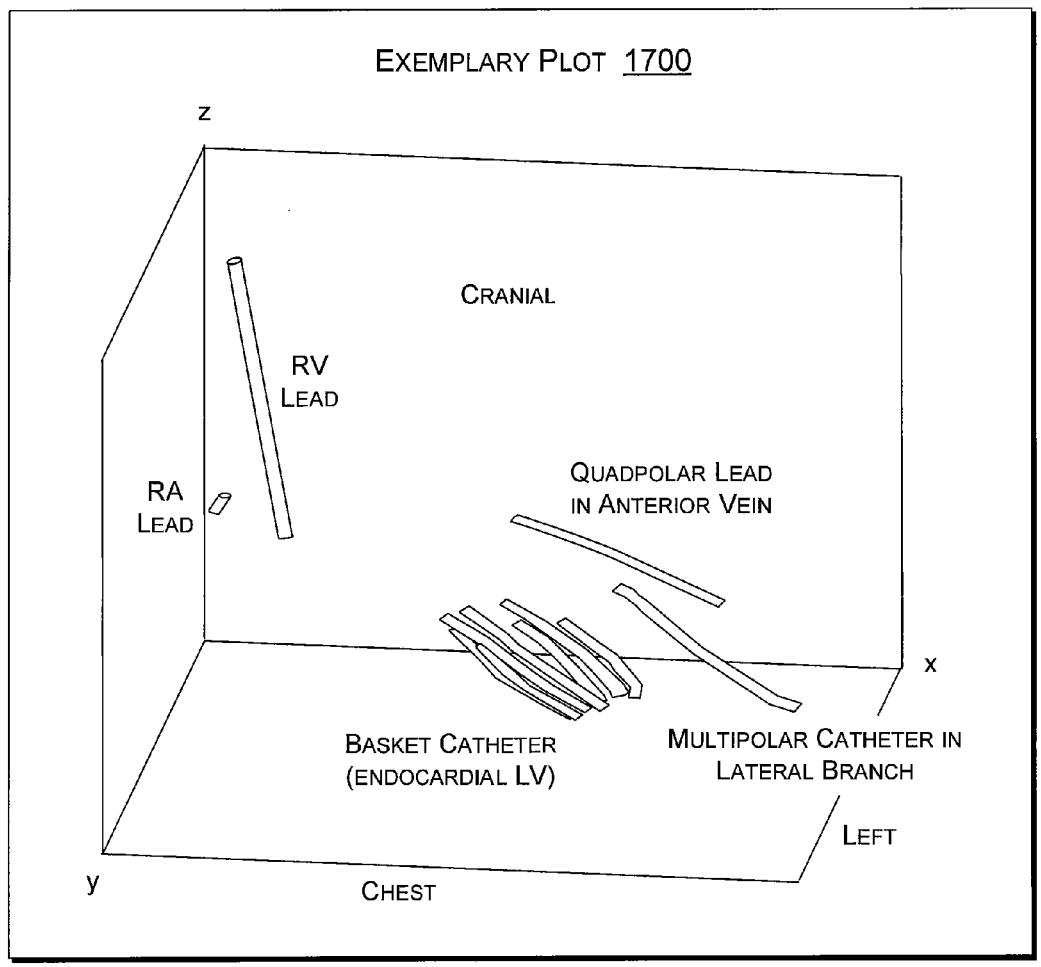
FIG. 17 is a plot of positions of various electrodes in and surrounding the heart.

FIG. 17 shows a plot 1700 of trial data acquired using a balloon catheter inserted into the left ventricle together with data acquired using epicardial electrodes positioned along the right ventricle, along the greater cardiac vein and along a lateral wall of the left ventricle. Volume of the electrodes is expanded to indicate swept volume as determined by extent of 3-D motion during a cardiac cycle.

As described herein, an exemplary method can include providing position with respect to time data for a plurality of electrodes, at least some of the electrodes located proximate to the right ventricle and at least some of the electrodes located proximate to the left ventricle; associating various of the electrodes as pairs along longitudes from the apex of the heart to the base of the heart where each pair includes an electrode located proximate to the right ventricle and an electrode located proximate to the left ventricle; for each pair, determining a longitudinal dyssynchrony metric; and determining a global dyssynchrony metric based on the longitudinal dyssynchrony metrics.

Longitudinal Shortening

FIG. 18 shows a diagram of the heart and an electrode arrangement corresponding to a long axis shortening scheme 1800 along with an exemplary method 1850 and an exemplary method 1870. In the example of FIG. 18, the electrode arrangement includes a left ventricular lead 1806, a right ventricular lead 1808, and a catheter 1815 for placement of the left ventricular lead 1806. In this scenario, during implantation of the LV lead 1806, the catheter 1815 includes a ring electrode 1817 at or proximate to its distal end that is placed at ostium of the coronary sinus. During pacing of LV (e.g., at a certain sinus rate), a long axis shortening metric can be determined based on motion data acquired for the catheter ring electrode 1817 and a tip electrode 1828 of the RV lead 1808.

Where the electrode 1817 has a corresponding vector $\vec{R}_1$ and where the electrode 1828 has a corresponding vector $\vec{R}_2$, the long axis distance between the catheter electrode 1817 and the RV lead electrode 1828 can be expressed as $\vec{L}$:

$$\vec{L} = \vec{R}_1 - \vec{R}_2$$

In the example of FIG. 18, $\vec{R}_1$ is the vector from an origin of a coordinate system to catheter electrode 1817 and $\vec{R}_2$ is the vector from the origin to the RV lead electrode 1828.

The exemplary method 1850 can determine a long axis shortening differential as $\Delta\vec{L}$, for example, as the difference between a maximum magnitude $|\vec{L}|_{max}$ Imax value and a minimum $|\vec{L}|_{min}$ value for a condition (e.g., CRT "on" or CRT "off"). Mathematically, this differential may be represented as follows:

$$|\Delta\vec{L}|=|\vec{L}|_{max}-|\vec{L}|_{min}$$

According to the exemplary method 1850, data is acquired in an acquisition block 1854. In a determination block 1858, a long axis differential is determined based on the acquired data. In an analysis block 1862, the method 1850 analyzes the long axis differential, for example, to decide whether a test condition improves mechanics of the heart as associated with the long axis.

An exemplary analysis determines $|\Delta\vec{L}|_A$ and $|\Delta\vec{L}|_B$ for a first condition A (e.g., CRT "off") and a second, different condition B (e.g., CRT "on"). Given $|\Delta\vec{L}|_A$ and $|\Delta\vec{L}|_B$ the analysis block 1862 may compare or subtract $|\Delta\vec{L}|_B$ from $|\Delta\vec{L}|_A$ such that when $|\Delta\vec{L}|_{A-B}<0$, that the patient is or likely to be a CRT responder. Further, the analysis block 1862 may decide, when $|\Delta\vec{L}|\rightarrow$MAX. Such an approach may be applied for optimization of CRT.

While the foregoing method refers to an electrode on the RV lead, with appropriate modifications, such a method may be applied to one or more LV lead electrodes (e.g., in conjunction with the electrode located at or near the coronary sinus).

In the exemplary method 1870, data is acquired in an acquisition block 1874. In a determination block 1878, a time to peak longitudinal shortening is determined for both an RV lead electrode and an LV lead electrode and the difference in time to peak longitudinal shortening between the RV electrode and the LV electrode. In an analysis or optimization block 1882, the time differential can be used alone or as an additional dyssynchrony metric to assess or optimize CRT. For instances where a multi-electrode catheter is positioned in the coronary sinus, the differential timing of longitudinal shortening between these electrodes in the coronary sinus moving toward the ostium or an atrial lead can yield a parameter similar to the mitral annular velocity, as measured by color tissue Doppler echocardiography.

As described herein, an exemplary method can include, for a first condition, providing position with respect to time data for a first electrode located proximate to the coronary sinus and for a second electrode located proximate to the apex of the right ventricle; for the first condition, determining a maximum displacement vector magnitude between the first electrode and the second electrode; for the first condition, determining a minimum displacement vector magnitude between the first electrode and the second electrode; for the first condition, determining a differential magnitude between the maximum displacement vector magnitude and the minimum displacement vector magnitude; for a second condition, providing position with respect to time data for the first electrode and for the second electrode; for the second condition, determining a maximum displacement vector magnitude between the first electrode and the second electrode; for the second condition, determining a minimum displacement vector magnitude between the first electrode and the second electrode; for the second condition, determining a differential magnitude between the maximum displacement vector magnitude and the minimum displacement vector magnitude; and deciding that the larger of the differential magnitudes corresponds to a condition that provides for better cardiac performance.

Exemplary External Programmer

Figure 19:
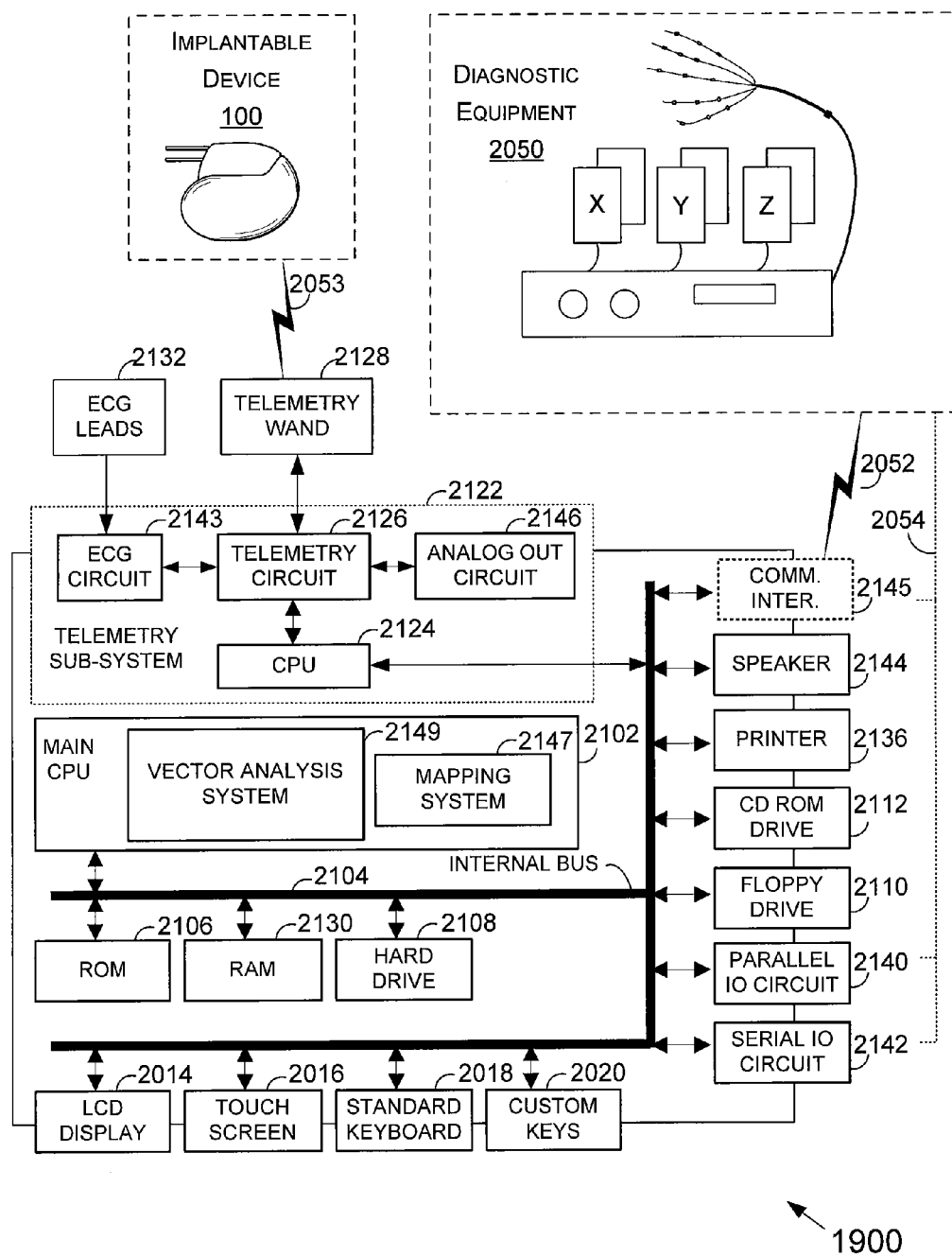
FIG. 19 is an exemplary system for acquiring information and analyzing such information.

FIG. 19 illustrates pertinent components of an external programmer 1900 for use in programming an implantable medical device 100 (see, e.g., FIGS. 1 and 2). The external programmer 1900 optionally receives information from other diagnostic equipment 1950, which may be a computing device capable of acquiring motion information related to cardiac mechanics. For example, the equipment 1950 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1900 in distinguishing respiratory motion from cardiac.

Briefly, the programmer 1900 permits a clinician or other user to program the operation of the implanted device 100 and to retrieve and display information received from the implanted device 100 such as IEGM data and device diagnostic data. Where the device 100 includes a module such as the motion module 239, then the programmer 1900 may instruct the device 100 to measure potentials and to communicate measured potentials to the programmer via a communication link 2053. The programmer 1900 may also instruct a device or diagnostic equipment to deliver current to generate one or more potential fields within a patient's body where the implantable device 100 may be capable of measuring potentials associated with the field(s).

The external programmer 1900 may be configured to receive and display ECG data from separate external ECG leads 2132 that may be attached to the patient. The programmer 1900 optionally receives ECG information from an ECG unit external to the programmer 1900. As already mentioned, the programmer 1900 may use techniques to account for respiration.

Depending upon the specific programming, the external programmer 1900 may also be capable of processing and analyzing data received from the implanted device 100 and from ECG leads 2132 to, for example, render diagnosis as to medical conditions of the patient or to the operations of the implanted device 100. As noted, the programmer 1900 is also configured to receive data representative of conduction time delays from the atria to the ventricles and to determine, therefrom, an optimal or preferred location for pacing. Further, the programmer 1900 may receive information such as ECG information, IEGM information, information from diagnostic equipment, etc., and determine one or more estimator (e.g., consider the method 300).

Now, considering the components of programmer 1900, operations of the programmer are controlled by a CPU 2102, which may be a generally programmable microprocessor or microcontroller or may be a dedicated processing device such as an application specific integrated circuit (ASIC) or the like. Software instructions to be performed by the CPU are accessed via an internal bus 2104 from a read only memory (ROM) 2106 and random access memory 2130. Additional software may be accessed from a hard drive 2108, floppy drive 2110, and CD ROM drive 2112, or other suitable permanent or removable mass storage device. Depending upon the specific implementation, a basic input output system (BIOS) is retrieved from the ROM 2106 by CPU 2102 at power up. Based upon instructions provided in the BIOS, the CPU 2102 "boots up" the overall system in accordance with well-established computer processing techniques.

Once operating, the CPU 2102 displays a menu of programming options to the user via an LCD display 2014 or other suitable computer display device. To this end, the CPU 2102 may, for example, display a menu of specific programming parameters of the implanted device 100 to be programmed or may display a menu of types of diagnostic data to be retrieved and displayed. In response thereto, the clinician enters various commands via either a touch screen 2016 overlaid on the LCD display or through a standard keyboard 2018 supplemented by additional custom keys 2020, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of the optimal pacing location, CPU 2102 includes a 3-D mapping system 2147 and a vector analysis system 2149. The systems 2147 and 2149 may receive mechanical information and electrical information from the implantable device 100 and/or diagnostic equipment 2050. The vector analysis system 2149 optionally includes control logic to associate information and to make one or more conclusions based on a measure such as the measures 330 of FIG. 3.

Where information is received from the implanted device 100, a telemetry wand 2128 may be used. Other forms of wireless communication exist as well as forms of communication where the body is used as a "wire" to communicate information from the implantable device 100 to the programmer 1900.

If information is received directly from diagnostic equipment 2050, any appropriate input may be used, such as parallel IO circuit 2140 or serial IO circuit 2142. Motion information received via the device 100 or via other diagnostic equipment 2050 may be analyzed using the mapping system 2147. In particular, the mapping system 2147 (e.g., control logic) may identify positions within the body of a patient and associate such positions with one or more electrodes where such electrodes may be capable of delivering stimulation energy to the heart.

A communication interface 2145 optionally allows for wired or wireless communication with diagnostic equipment 2050 or other equipment. The communication interface 2145 may be a network interface connected to a network (e.g., intranet, Internet, etc.).

A map or model of cardiac motion may be displayed using display 2014 based, in part, on 3-D heart information and optionally 3-D torso information that facilitates interpretation of motion information. Such 3-D information may be input via ports 2140, 2142, 2145 from, for example, a database, a 3-D imaging system, a 3-D location digitizing apparatus (e.g., stereotactic localization system with sensors and/or probes) capable of digitizing the 3-D location. According to such an example, a clinician can thereby view the optimal location for delivery of stimulation energy on a map of the heart to ensure that the location is acceptable before an electrode or electrodes are positioned and optionally fixed at that location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1900 optionally records procedures and allows for playback (e.g., for subsequent review). For example, a heart map and all of the electrical activation data, mechanical activation data, VE data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 2122 may include its own separate CPU 2124 for coordinating the operations of the telemetry subsystem. In a dual CPU system, the main CPU 2102 of programmer communicates with telemetry subsystem CPU 2124 via internal bus 2104. Telemetry subsystem additionally includes a telemetry circuit 2126 connected to telemetry wand 2128, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1900 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1900 (e.g., within a random access memory (RAM) 2130, hard drive 2108, within a floppy diskette placed within floppy drive 2110). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1900 has a communication link to an external storage device or network storage device, then information may be stored in such a manner (e.g., on-site database, off-site database, etc.). The programmer 1900 optionally receives data from such storage devices.

A typical procedure may include transferring all patient and device diagnostic data stored in an implanted device 100 to the programmer 1900. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 2122 receives ECG signals from ECG leads 2132 via an ECG processing circuit 2134. As with data retrieved from the implanted device 100, signals received from the ECG leads are stored within one or more of the storage devices of the programmer 1900. Typically, ECG leads output analog electrical signals representative of the ECG. Accordingly, ECG circuit 2134 includes analog to digital conversion circuitry for converting the signals to digital data appropriate for further processing within programmer 1900. Depending upon the implementation, the ECG circuit 2143 may be configured to convert the analog signals into event record data for ease of processing along with the event record data retrieved from the implanted device. Typically, signals received from the ECG leads 2132 are received and processed in real time.

Thus, the programmer 1900 is configured to receive data from a variety of sources such as, but not limited to, the implanted device 100, the diagnostic equipment 2050 and directly or indirectly via external ECG leads (e.g., subsystem 2122 or external ECG system). The diagnostic equipment 2050 includes wired 2054 and/or wireless capabilities 2052 which optionally operate via a network that includes the programmer 1900 and the diagnostic equipment 2050 or data storage associated with the diagnostic equipment 2050.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 2102, the programming commands are converted to specific programming parameters for transmission to the implanted device 100 via telemetry wand 2128 to thereby reprogram the implanted device 100 or other devices, as appropriate.

Prior to reprogramming specific parameters, the clinician may control the external programmer 1900 to display any or all of the data retrieved from the implanted device 100, from the ECG leads 2132, including displays of ECGs, IEGMs, statistical patient information (e.g., via a database or other source), diagnostic equipment 2050, etc. Any or all of the information displayed by programmer may also be printed using a printer 2136.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1900 optionally includes a modem to permit direct transmission of data to other programmers via the public switched telephone network (PSTN) or other interconnection line, such as a T1 line or fiber optic cable. Depending upon the implementation, the modem may be connected directly to internal bus 2104 may be connected to the internal bus via either a parallel port 2140 or a serial port 2142.

Other peripheral devices may be connected to the external programmer via the parallel port 2140, the serial port 2142, the communication interface 2145, etc. Although one of each is shown, a plurality of input output (IO) ports might be provided. A speaker 2144 is included for providing audible tones to the user, such as a warning beep in the event improper input is provided by the clinician. Telemetry subsystem 2122 additionally includes an analog output circuit 2146 for controlling the transmission of analog output signals, such as IEGM signals output to an ECG machine or chart recorder.

With the programmer 1900 configured as shown, a clinician or other user operating the external programmer is capable of retrieving, processing and displaying a wide range of information received from the ECG leads 2132, from the implanted device 100, the diagnostic equipment 2050, etc., and to reprogram the implanted device 100 or other implanted devices if needed. The descriptions provided herein with respect to FIG. 19 are intended merely to provide an overview of the operation of programmer and are not intended to describe in detail every feature of the hardware and software of the device and is not intended to provide an exhaustive list of the functions performed by the device.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method of characterizing motion of a first electrode implanted along a lateral wall of the left ventricle and a second electrode implanted along a septal wall between the right ventricle and the left ventricle, said method comprising:
    for a time in a cardiac cycle, determining a three-dimensional position of the first implanted electrode and a three-dimensional position of the second implanted electrode;
    for another time in a cardiac cycle, determining a three-dimensional position of the first implanted electrode and a three-dimensional position of the second implanted electrode;
    determining a first vector differential based on a vector for the first implanted electrode for the time in the cardiac cycle and another vector for the first implanted electrode for the other time in the cardiac cycle;
    determining a second vector differential based on a vector for the second implanted electrode for the time in the cardiac cycle and another vector for the second implanted electrode for the other time in the cardiac cycle;
    calculating the dot product of the first vector differential and the second vector differential; and
    if the dot product is less than zero, determining that the first electrode and the second electrode either move toward each other or away from each other.

2. The method of claim 1 wherein the times in the cardiac cycle comprise times during systole and further comprising repeating the method for times during diastole and deciding whether the dot product is greater than zero for the times during systole and whether the dot product is greater than zero for the times during diastole; and
    if the dot product is greater than zero for the times during systole and for the times during diastole, determining that the motion of the first electrode and the second electrode indicates dyssynchrony of cardiac motion.

3. The method of claim 1 further comprising, for the time in a cardiac cycle, determining, over multiple cardiac cycles, a three-dimensional position of the first implanted electrode and a three-dimensional position of the second implanted electrode wherein the position of the first implanted electrode at the time comprises an average of multiple positions and wherein the position of the second implanted electrode at the time comprises an average of multiple positions.

4. The method of claim 1 further comprising, for the other time in a cardiac cycle, determining, over multiple cardiac cycles, a three-dimensional position of the first implanted electrode and a three-dimensional position of the second implanted electrode wherein the position of the first implanted electrode at the other time comprises an average of multiple positions and wherein the position of the second implanted electrode at the other time comprises an average of multiple positions.

5. The method of claim 1 further comprising performing the method for more than two times in a cardiac cycle.

6. A method of characterizing motion of a first electrode implanted along a lateral wall of the left ventricle and a second electrode implanted along a septal wall between the right ventricle and the left ventricle, said method comprising:
- for a time in a cardiac cycle, determining a three-dimensional position of the first implanted electrode and a three-dimensional position of the second implanted electrode;
- for another time in a cardiac cycle, determining a three-dimensional position of the first implanted electrode and a three-dimensional position of the second implanted electrode;
- determining a first vector differential based on a vector for the first implanted electrode for the time in the cardiac cycle and another vector for the first implanted electrode for the other time in the cardiac cycle;
- determining a second vector differential based on a vector for the second implanted electrode for the time in the cardiac cycle and another vector for the second implanted electrode for the other time in the cardiac cycle;
- deciding whether the first vector differential and the second vector differential are approximately zero; and
- if the first vector differential and the second vector differential are approximately zero, determining that a condition applied to the heart does not affect cardiac synchrony.

7. The method of claim 6 wherein the condition applied to the heart comprises cardiac resynchronization therapy (CRT).

8. A method of characterizing motion of a first electrode implanted along a lateral wall of the left ventricle and a second electrode implanted along a septal wall between the right ventricle and the left ventricle, said method comprising:
- for a time in a cardiac cycle, determining a three-dimensional position of the first implanted electrode and a three-dimensional position of the second implanted electrode;
- for another time in a cardiac cycle, determining a three-dimensional position of the first implanted electrode and a three-dimensional position of the second implanted electrode;
- determining a first vector differential based on a vector for the first implanted electrode for the time in the cardiac cycle and another vector for the first implanted electrode for the other time in the cardiac cycle;
- determining a second vector differential based on a vector for the second implanted electrode for the time in the cardiac cycle and another vector for the second implanted electrode for the other time in the cardiac cycle;
- determining the magnitude of the first vector differential and the magnitude of the second vector differential;
- summing the magnitudes; and
- deciding whether the sum of the magnitudes is greater than a previously determined sum of magnitudes for the first implanted electrode and the second implanted electrode.

9. A method of characterizing motion of a first electrode implanted along a lateral wall of the left ventricle and a second electrode implanted along a septal wall between the right ventricle and the left ventricle, said method comprising:
- for a time in a cardiac cycle, determining a three-dimensional position of the first implanted electrode and a three-dimensional position of the second implanted electrode;
- for another time in a cardiac cycle, determining a three-dimensional position of the first implanted electrode and a three-dimensional position of the second implanted electrode;
- determining a first vector differential based on a vector for the first implanted electrode for the time in the cardiac cycle and another vector for the first implanted electrode for the other time in the cardiac cycle;
- determining a second vector differential based on a vector for the second implanted electrode for the time in the cardiac cycle and another vector for the second implanted electrode for the other time in the cardiac cycle;
- determining a measure of the relative motion between the first electrode and the second electrode based on the of the first vector differential and the second vector differential; and
- deciding whether the measure is greater than a previously determined measure.

10. A method of characterizing motion of a first electrode implanted along a lateral wall of the left ventricle and a second electrode implanted along a septal wall between the right ventricle and the left ventricle, said method comprising:
- for a time in a cardiac cycle, determining a three-dimensional position of the first implanted electrode and a three-dimensional position of the second implanted electrode;
- for another time in a cardiac cycle, determining a three-dimensional position of the first implanted electrode and a three-dimensional position of the second implanted electrode;
- determining a first vector differential based on a vector for the first implanted electrode for the time in the cardiac cycle and another vector for the first implanted electrode for the other time in the cardiac cycle;
- determining a second vector differential based on a vector for the second implanted electrode for the time in the cardiac cycle and another vector for the second implanted electrode for the other time in the cardiac cycle;
- processing the first vector differential and the second vector differential to provide a measurement of the motion of one or more of the first implanted electrode and the second implanted electrode;
- performing the foregoing steps for a plurality of therapy conditions to obtain a corresponding plurality of measurements;
- comparing the plurality of measurements; and
- determining an optimal therapy condition based on the comparison;
- wherein the plurality of measurements correspond to summations of the absolute values of the first differential vector and the second differential vector and the optimal therapy condition correspond to the maximum measurement.

11. A method of characterizing motion of a first electrode implanted along a lateral wall of the left ventricle and a second electrode implanted along a septal wall between the right ventricle and the left ventricle, said method comprising:
- for a time in a cardiac cycle, determining a three-dimensional position of the first implanted electrode and a three-dimensional position of the second implanted electrode;
- for another time in a cardiac cycle, determining a three-dimensional position of the first implanted electrode and a three-dimensional position of the second implanted electrode;

determining a first vector differential based on a vector for the first implanted electrode for the time in the cardiac cycle and another vector for the first implanted electrode for the other time in the cardiac cycle;

determining a second vector differential based on a vector for the second implanted electrode for the time in the cardiac cycle and another vector for the second implanted electrode for the other time in the cardiac cycle;

processing the first vector differential and the second vector differential to provide a measurement of the motion of one or more of the first implanted electrode and the second implanted electrode;

performing the foregoing steps for a plurality of therapy conditions to obtain a corresponding plurality of measurements;

comparing the plurality of measurements; and determining an optimal therapy condition based on the comparison;

wherein the plurality of measurements correspond to the number of times during a common time period that the dot product of the first differential vector and the second differential vector is less than zero and the optimal therapy condition correspond to the maximum measurement.

12. The method of claim 11 wherein therapy conditions comprise one or more of different electrode locations, different pacing parameters and different pacing interventions.

13. A method comprising:
providing a feature time corresponding to the appearance of a feature of electrical activity during a cardiac cycle;
providing a time, during the cardiac cycle, corresponding to a peak three-dimensional position of an electrode located along a septal wall between the right ventricle and the left ventricle;
providing a time, during the cardiac cycle, corresponding to a peak three-dimensional position of an electrode located along a lateral wall of the left ventricle;
for the cardiac cycle, with respect to the feature time, determining a septal-to-lateral-wall time delay as a difference between the time of the peak position of the electrode located along the lateral wall and the time of the peak position of the electrode located along the septal wall; and
based on the difference, deciding whether, during the cardiac cycle, cardiac motion was dyssynchronous.

14. The method of claim 13 wherein deciding cardiac motion was dyssynchronous comprises determining that the septal-to-lateral-wall time delay is either greater than a predetermined positive limit or less than a predetermined negative limit.

15. The method of claim 13 further comprising repeating the providings and the determining for multiple cardiac cycles.

16. The method of claim 13 further comprising, if the deciding decides that the cardiac motion was dyssynchronous during the cardiac cycle, calling for delivery of a cardiac pacing therapy.

17. The method of claim 13 wherein the cardiac cycle comprises a paced cardiac cycle associated with a cardiac pacing therapy.

18. The method of claim 17 wherein if the deciding decides that the cardiac motion was dyssynchronous during the cardiac cycle, calling for optimization of the cardiac pacing therapy.

19. The method of claim 18 wherein the optimization optimizes the cardiac pacing therapy by reducing the septal to lateral wall time delay.

20. A method comprising:
for a cardiac cycle, determining a septal-to-lateral-wall time delay as a difference between a time of a peak three-dimensional position of an electrode located along the lateral wall and a time of a peak three-dimensional position of an electrode located along the septal wall;
determining a peak velocity for at least one of the electrodes; and
adjusting a cardiac pacing therapy to minimize the time delay and to maximize the peak velocity.

21. The method of claim 20 further comprising determining a peak velocity for both of the electrodes.

22. The method of claim 21 wherein the adjusting adjusts a cardiac pacing therapy from performing single ventricle pacing to performing biventricular pacing.

23. A method comprising:
providing position-with-respect-to-time data for a plurality of electrodes, at least some of the electrodes located proximate to the right ventricle and at least some of the electrodes located proximate to the left ventricle;
associating various of the electrodes as pairs along longitudes from the apex of the heart to the base of the heart wherein each pair comprises an electrode located proximate to the right ventricle and an electrode located proximate to the left ventricle;
for each pair, determining a longitudinal dyssynchrony metric based on the position-with-respect-to-time data for each electrode in the pair; and
determining a global dyssynchrony metric based on the longitudinal dyssynchrony metrics.

24. The method of claim 23 wherein the position-with-respect-to-time data is the time to peak displacement of the electrode and the longitudinal dyssynchrony metric corresponds to the difference between the time to peak displacements of the electrodes in the pair.

25. A method comprising:
for a first condition, providing position-with-respect-to-time data for a first electrode located proximate to the coronary sinus and for a second electrode located proximate to the apex of the right ventricle;
for the first condition, determining a maximum displacement vector magnitude between the first electrode and the second electrode;
for the first condition, determining a minimum displacement vector magnitude between the first electrode and the second electrode;
for the first condition, determining a differential magnitude between the maximum displacement vector magnitude and the minimum displacement vector magnitude;
for a second condition, providing position-with-respect-to-time data for the first electrode and for the second electrode;
for the second condition, determining a maximum displacement vector magnitude between the first electrode and the second electrode;
for the second condition, determining a minimum displacement vector magnitude between the first electrode and the second electrode;
for the second condition, determining a differential magnitude between the maximum displacement vector magnitude and the minimum displacement vector magnitude; and
deciding that the larger of the differential magnitudes corresponds to a condition that provides for better cardiac performance.

* * * * *